United States Patent
Green et al.

(10) Patent No.: US 9,173,938 B2
(45) Date of Patent: Nov. 3, 2015

(54) COMBINATION OF A PURINE-BASED CDK INHIBITOR WITH A TYROSINE KINASE INHIBITOR AND USE THEREOF IN THE TREATMENT OF PROLIFERATIVE DISORDERS

(75) Inventors: Simon Green, Dundee (GB); Sheelagh Frame, Dundee (GB); Ian Fleming, Angus (GB)

(73) Assignee: Cyclacel Limited, London (GB)

( * ) Notice: Subject to any disclaimer, the term of this patent is extended or adjusted under 35 U.S.C. 154(b) by 142 days.

(21) Appl. No.: 12/573,358

(22) Filed: Oct. 5, 2009

(65) Prior Publication Data
US 2010/0143350 A1 Jun. 10, 2010

Related U.S. Application Data

(63) Continuation of application No. PCT/GB2008/001189, filed on Apr. 2, 2008.

(60) Provisional application No. 60/921,699, filed on Apr. 4, 2007.

(30) Foreign Application Priority Data

Apr. 4, 2007 (GB) .................................. 0706633.5

(51) Int. Cl.
| C07D 473/34 | (2006.01) |
| A61K 31/52 | (2006.01) |
| A61K 45/06 | (2006.01) |
| A61K 31/517 | (2006.01) |

(52) U.S. Cl.
CPC ............... A61K 45/06 (2013.01); A61K 31/517 (2013.01); A61K 31/52 (2013.01)

(58) Field of Classification Search
CPC .. C07D 473/34; C07D 473/16; C07D 473/00; A61K 31/52
USPC .............. 514/235.8, 255.05, 263.4, 283, 364, 514/263.22; 424/133.1
See application file for complete search history.

(56) References Cited

U.S. PATENT DOCUMENTS

2005/0272755 A1* 12/2005 Denis et al. .................... 514/283
2007/0270438 A1* 11/2007 Bhattacharya et al. .. 514/255.05
2009/0306098 A1* 12/2009 Green et al. ............... 514/263.4

FOREIGN PATENT DOCUMENTS

| GB | 2392155 | 2/2004 |
| JP | 2006-506341 | 2/2006 |
| WO | WO-97/20842 A1 | 6/1997 |
| WO | 2004/016612 A2 | 2/2004 |
| WO | 2004/041308 A1 | 5/2004 |

OTHER PUBLICATIONS

Cascone et al. (Annals of Oncology, Mar. 2006, 17 (Supplement 2): ii46-ii48).*
PubChem Compound, NCBI, Oct. 25, 2011.*
Buck et al. (Mol Cancer Ther 2006, 5: 2676-2684).*
Fischer et al. (Expert Opin. Investig. Drugs, 2005, 14(4): 457-477).*
Stratagene Catalog 1988, p. 39.*
Azim, Hatem A., Jr. et al., "Targeted therapy in advanced non-small cell lung cancer (NSCLC): Where do we stand?," Cancer Treatment Reviews, vol. 32:630-636 (2006).
Dancey, Janet E. et al., "Strategies for optimizing combinations of molecularly targeted anticancer agents," Nature Reviews/Drug Discovery, vol. 5:649-659 (2006).
Fleming, Ian N. et al., "Combination analysis between seliciclib (CYC202; R-roscovitine) and other molecularly targeted anti-cancer agents in non-small cell lung cancer," Proceedings of the American Association for Cancer Research, vol. 47:902-903 (2006).
Frame, Sheelagh et al., "Synergistic Combinations Between the Oral CDK Inhibitor, Seliciclib, and EGFR Inhibitors in NSCLC," Centennial AACR Annual Meeting, Abstract No. 4003 (2007).
Shah, Manish A. et al., "Cyclin dependent kinases as targets for cancer therapy," Update on Cancer Therapeutics I, vol. 1(3):311-332 (2006).
Speake, Georgina et al., "Recent developments related to the EGFR as a target for cancer chemotherapy," Current Opinion in Pharmacology, vol. 5:343-349 (2005).
Ali, Shadan et al., "Sequence dependent potentiation of gemcitabine by flavopiridol in human breast cancer cells," Breast Cancer Research and Treatment, vol. 90:25-31 (2005).
Dai, Yun et al., "Cyclin-dependent kinase inhibitors," Current Opinion in Pharmacology, vol. 3:362-370 (2003).
Fischer, Peter M., "The Use of CDK Inhibitors in Oncology," Cell Cycle, vol. 3(6):742-746 (2004).
Knockaert, Marie et al., "Pharmacological inhibitors of cyclin-dependent kinases," Trends in Pharmacological Sciences, vol. 23(9):417-425 (2002).
Leost, Maryse et al., "Paullones are potent inhibitors of glycogen synthase kinase-3beta and cyclin-dependent kinase 5/p25," Eur. J. Biochem., vol. 267:5983-5994 (2000).

(Continued)

Primary Examiner — Yan Xiao
(74) Attorney, Agent, or Firm — Nelson Mullins Riley & Scarborough LLP; Cynthia L. Kanik

(57) ABSTRACT

The present invention relates to combination comprising (i) an ErbB inhibitor; and (ii) a CDK inhibitor, or a pharmaceutically acceptable salt thereof, selected from: (a) roscovitine; (b) 3-{9-isopropyl-6-[(pyridin-3-ylmethyl)-amino]-9H-purin-2-ylamino}-2-methyl-pentan-2-ol; (c) 3-{9-isopropyl-6-[(pyridin-3-ylmethyl)-amino]-9H-purin-2-ylamino}-pentan-2-ol; and (d) (2R,3S-3-(6-((4,6-dimethylpyridin-3-ylmethylamino)-9-isopropyl-9H-purin-2-ylamino)pentan-2-ol.

Figure 1:
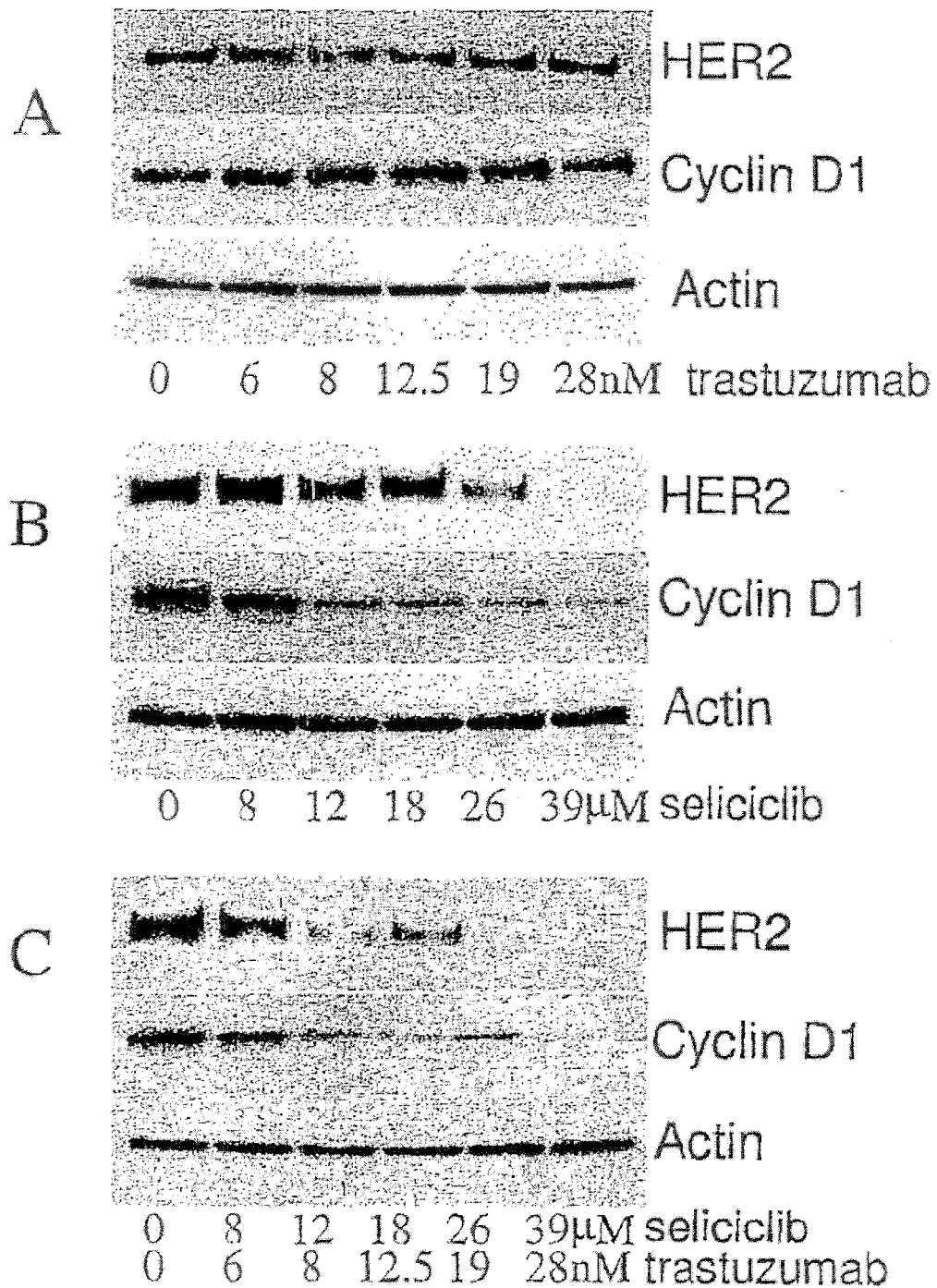

Further aspects of the invention relate to pharmaceutical products and pharmaceutical compositions comprising combinations according to the invention, and methods of treatment using the same.

19 Claims, 6 Drawing Sheets

(56) References Cited

OTHER PUBLICATIONS

MacCallum, David E. et al., "Seliciclib (CYC202, R-Roscovitine) Induces Cell Dealth in Multiple Myeloma Cells by Inhibition of RNA Polymerase II-Dependent Transcription and Down-regulation of Mcl-1," Cancer Research, vol. 65 (12):5399-5407 (2005).

Meijer, Laurent et al., "Chemical inhibitors of cyclin-dependent kinases," Trends in Cell Biology, vol. 6:393-397 (1996).

Villerbu, Nathalie et al., "Cellular Effects of Purvalanol A: A Specific Inhibitor of Cyclin-dependent Kinase Activities," Int. J. Cancer, vol. 97:761-769 (2002).

* cited by examiner

A549  H460  H358

EGFR pERK

ERK pPKB

PKB

Fig. 2

COMBINATION OF A PURINE-BASED CDK INHIBITOR WITH A TYROSINE KINASE INHIBITOR AND USE THEREOF IN THE TREATMENT OF PROLIFERATIVE DISORDERS

RELATED APPLICATIONS

This application is a continuation of PCT/GB2008/001189, which was filed on Apr. 2, 2008 and which claims priority to GB 0706633.5, which was filed on Apr. 4, 2007, and to U.S. 60/921,699, which was filed on Apr. 4, 2007. The entire contents of each of these applications are hereby incorporated herein by reference.

FIELD OF INVENTION

The present invention relates to a pharmaceutical combination suitable for the treatment of cancer and other proliferative disorders.

BACKGROUND

Protein kinases are key regulators of essential cellular processes, and because they contain a distinct active site, thereby allowing compound binding, kinases are an attractive area for anti-cancer drug discovery [1]. However, it was not until the successful clinical development of imatinib, targeting BCR-ABL, that the first targeted protein kinase inhibitor became an approved cancer chemotherapeutic [2]. Currently protein kinases are a very active area for cancer drug discovery with many protein kinase families being the focus of drug development programs. Such discovery programs often target signalling pathways that become deregulated during tumour development.

Members of the ErbB family, like many other growth factor receptors, dimerise upon ligand stimulation and undergo autophosphorylation through their cytoplasmic tyrosine kinase domains. Once activated, the ErbB kinases transduce their signals via a number of cellular protein kinases, including ERK and PKB, to ultimately result in upregulation of Cyclin D1 levels leading to activation of cyclin dependent kinases (CDKs) and the initiation of cellular proliferation [3]. Over-stimulation of ErbB receptor tyrosine kinase signalling has been documented in a number of different human cancers, including overexpression of HER2 (ErbB2) in up to 30% of breast cancer patients [4], while EGFR (ErbB1) is overexpressed in ovarian carcinomas (35-60%), head and neck tumours (70-100%) and non-small cell lung cancer (NSCLC; 50-90%) [5, 6]. Two main approaches have been pursued for the development of drugs that target the ErbB family. Humanised monoclonal antibodies such as trastuzumab and cetuximab bind to the HER2 and EGF receptors respectively, thereby blocking receptor dimerization/activation and facilitating removal of these proteins from the cell surface [3]. In contrast, erlotinib and gefitinib are small molecules that bind directly to the ATP-binding active site of the EGFR, blocking tyrosine kinase activity [7]. For each of these agents, the subsequent loss of mitogenic signalling results in the cessation of cellular proliferation.

The CDKs are a second kinase family that have attracted a considerable amount of interest from a drug discovery perspective; with the three most advanced compounds, seliciclib (CYC202, R-roscovitine), alvocidib (flavopiridol) and SNS-032 (formerly BMS-387032) all currently in Phase II clinical development [8, 9]. Through their key role of phosphorylating proteins involved in the regulation of cell cycle checkpoints, CDKs control the orderly progression of the cell division cycle [8]. In cancer cells activation of CDKs by either overexpression of their cognate partners, the cyclins, or loss of the endogenous inhibitors such as p16 leads to inappropriate proliferation of cells that would normally be arrested and either repaired or induced to undergo apoptosis at specific cell cycle checkpoints [10]. In addition to controlling the cell cycle, some CDKs, such as CDK7 and CDK9, regulate transcription by phosphorylating the carboxy-terminal domain of RNA polymerase II. Seliciclib, alvocidib and SNS-032 all inhibit CDK7 and/or 9 thereby leading to the inhibition of transcription, and downregulation of proteins such as Mcl-1 and cyclin D1 [11, 12], which have short half-lives of approximately 3 h and 30 min respectively [13, 14].

The present invention seeks to provide new combinations that have therapeutic applications in the treatment of a range of proliferative disorders, more particularly cancer.

STATEMENT OF INVENTION

A first aspect relates to a combination comprising (i) an ErbB inhibitor; and (ii) a CDK inhibitor, or a pharmaceutically acceptable salt thereof, selected from: (a) roscovitine; (b) 3-{9-isopropyl-6-[(pyridin-3-ylmethyl)-amino]-9H-purin-2-ylamino}-2-methyl-pentan-2-ol; (c) 3-{9-isopropyl-6-[(pyridin-3-ylmethyl)-amino]-9H-purin-2-ylamino}-pentan-2-ol; and (d) (2R,3S-3-(6-((4,6-dimethylpyridin-3-ylmethylamino)-9-isopropyl-9H-purin-2-ylamino)pentan-2-ol.

A second aspect relates to a pharmaceutical composition comprising a combination according to the invention and a pharmaceutically acceptable carrier, diluent or excipient.

A third aspect related to a pharmaceutical product comprising (i) an ErbB inhibitor; and (ii) a CDK inhibitor, or a pharmaceutically acceptable salt thereof, selected from: (a) roscovitine; (b) 3-{9-isopropyl-6-[(pyridin-3-ylmethyl)-amino]-9H-purin-2-ylamino}-2-methyl-pentan-2-ol; (c) 3-{9-isopropyl-6-[(pyridin-3-ylmethyl)-amino]-9H-purin-2-ylamino}-pentan-2-ol; and (d) (2R,3S-3-(6-((4,6-dimethylpyridin-3-ylmethylamino)-9-isopropyl-9H-purin-2-ylamino)pentan-2-ol as a combined preparation for simultaneous, sequential or separate use in therapy.

A fourth aspect relates to a method of treating a proliferative disorder, said method comprising simultaneously, sequentially or separately administering to a subject (i) an ErbB inhibitor; and (ii) a CDK inhibitor, or a pharmaceutically acceptable salt thereof, selected from: (a) roscovitine; (b) 3-{9-isopropyl-6-[(pyridin-3-ylmethyl)-amino]-9H-purin-2-ylamino}-2-methyl-pentan-2-ol; (c) 3-{9-isopropyl-6-[(pyridin-3-ylmethyl)-amino]-9H-purin-2-ylamino}-pentan-2-ol; and (d) (2R,3S-3-(6-((4,6-dimethylpyridin-3-ylmethylamino)-9-isopropyl-9H-purin-2-ylamino)pentan-2-ol.

A fifth aspect relates to a method of treating non-small cell lung cancer (NSCLC), said method comprising simultaneously, sequentially or separately administering to a subject (i) an ErbB inhibitor; and (ii) a CDK inhibitor, or a pharmaceutically acceptable salt thereof, selected from: (a) roscovitine; (b) 3-{9-isopropyl-6-[(pyridin-3-ylmethyl)-amino]-9H-purin-2-ylamino}-2-methyl-pentan-2-ol; (c) 3-{9-isopropyl-6-[(pyridin-3-ylmethyl)-amino]-9H-purin-2-ylamino}-pentan-2-ol; and (d) (2R,3S-3-(6-((4,6-dimethylpyridin-3-ylmethylamino)-9-isopropyl-9H-purin-2-ylamino)pentan-2-ol.

A sixth aspect relates to a kit of parts comprising:
(i) an ErbB inhibitor; and
(ii) a CDK inhibitor, or a pharmaceutically acceptable salt thereof, selected from: (a) roscovitine; (b) 3-{9-isopropyl-6-[(pyridin-3-ylmethyl)-amino]-9H-purin-2-ylamino}-2-methyl-pentan-2-ol; (c) 3-{9-isopropyl-6-[(pyridin-3-yl-methyl)-amino]-9H-purin-2-ylamino}-pentan-2-ol; and
(d) (2R,3S-3-(6-((4,6-dimethylpyridin-3-ylmethylamino)-9-isopropyl-9H-purin-2-ylamino)pentan-2-ol.

A further aspect of the invention relates to a combination comprising (i) an ErbB inhibitor; and (ii) a compound of formula I, or a pharmaceutically acceptable salt thereof,

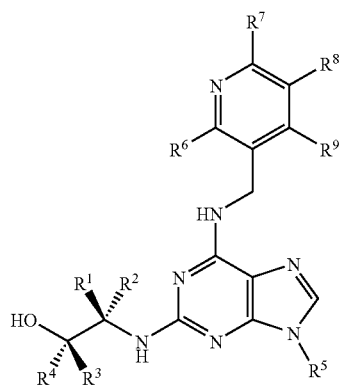

(I)

wherein:
$R^1$ and $R^2$ are each independently H or alkyl;
$R^3$ and $R^4$ are each independently H, alkyl or aryl;
$R^5$ is alkyl or cycloalkyl, each of which may be optionally substituted with one or more OH groups;
$R^6$, $R^7$, $R^8$ and $R^9$ are each independently H, alkyl, haloalkyl, halogen, $NO_2$, OH, OMe, CN, $NH_2$, COOH, $CONH_2$, or $SO_2NH_2$.

Further aspects of the invention relate to pharmaceutical products, pharmaceutical compositions and a kit of parts comprising said combination, and methods of treatment using the same.

DETAILED DESCRIPTION

The preferred embodiments set out below are applicable to all the above-mentioned aspects of the invention.

As mentioned above, the present invention relates to a combination comprising an ErbB inhibitor and a CDK inhibitor as set forth above.

In one preferred embodiment, the ErbB inhibitor is an ErbB1 (EGFR) inhibitor.

Preferably, the EGFR inhibitor is selected from AG1478, cetuximab, erlotinib, gefitinib, lapatinib, panitumumab, matuzumab, nimotuzumab, zalutumumab, pertuzumab, canertinib, vandetanib, EKB-569, HKI-272, BIBW-2992, AEE-788, XL647, BMS-599626, PKI-116 and ARRY-334543.

More preferably, the EGFR inhibitor is selected from AG1478, cetuximab, erlotinib, gefitinib and lapatinib.

In another preferred embodiment, the ErbB inhibitor is an ErbB2 (Her2) inhibitor. More preferably, the ErbB2 inhibitor is trastuzumab.

In one preferred embodiment, the ErbB inhibitor targets both Her2 and EGFR (for example, lapatinib, canertinib, EKB-569, HKI-272, BIBW-2992, AEE-788, XL647, BMS-599626, PKI-116 and ARRY-334543).

In one preferred embodiment, the ErbB inhibitor is selected from AG1478, trastuzumab, cetuximab, erlotinib, gefitinib, lapatinib, panitumumab, matuzumab, nimotuzumab, zalutumumab, pertuzumab, canertinib, vandetanib, EKB-569, HKI-272, BIBW-2992, AEE-788, XL647, BMS-599626, PKI-116, ARRY-334543.

More preferably, the ErbB inhibitor is selected from AG1478, trastuzumab, cetuximab, erlotinib, gefitinib and lapatinib.

In one particularly preferred embodiment, the EGFR inhibitor is AG1478.

AG1478 [4-(3-chloroanilino)-6,7-dimethoxyquinazoline] is a reversible, highly potent ($IC_{50}$=3 nM) and selected inhibitor of EGFR tyrosine kinase activity, commonly used as an EGF signalling blocker (www.alomone.com). The chemical structure of AG1478 is:

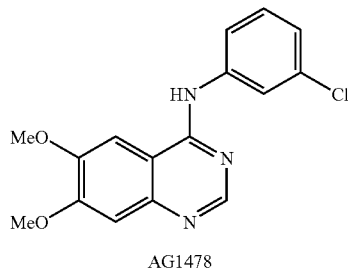 [SMILES: COc1cc2ncnc(Nc3cccc(Cl)c3)c2cc1OC]

AG1478

In another particularly preferred embodiment, the ErbB inhibitor is trastuzumab.

As mentioned above, trastuzumab (Herceptin®) is a recombinant DNA-derived humanized monoclonal antibody that selectively binds with high affinity in a cell-based assay (Kd=5 nM) to the extracellular domain of the human epidermal growth factor receptor 2 protein, HER2 (Coussens, L. et al., Science, 1985; 230: 1132-9; Slamon, D. J. et al., Science, 1989; 244:707-12). The antibody is an $IgG_1$ kappa that contains human framework regions with the complementarity-determining regions of a murine antibody (4D5) that binds to HER2.

For monotherapy, trastuzumab is indicated for the treatment of patients with metastatic breast cancer whose tumours overexpress the HER2 protein and who have received one or more chemotherapy regimens for the metastatic disease. Trastuzumab has also been approved for use in combination with paclitaxel for treatment of patients with metastatic breast cancer whose tumours overexpress the HER2 protein and who have not received chemotherapy for their metastatic disease.

Studies by the applicant investigated the effect of seliciclib and trastuzumab in combination in a breast cancer cell line that overexpresses the HER2 receptor. In addition, the interaction between seliciclib and the tyrphostin AG1478 was examined to determine whether synergy occurred between CDK inhibitors and small molecule inhibitors of the EGFR tyrosine kinase [18]. The results demonstrated that seliciclib synergised with trastuzumab in the breast cancer cell line SkBr3 that overexpresses HER2. Seliciclib also synergised with AG1478 in the NSCLC cell lines H358 and H1650 which express wild type and mutant EGFR respectively. In each case synergy involved inhibition of the HER2/EGFR signalling pathways. These in vitro findings were further expanded to demonstrate that the combination between seliciclib and erlotinib was synergistic in an H358 xenograft model. The data presented herein show that combinations between seliciclib and inhibitors of the ErbB receptor family can result in synergistic effects on cancer cell growth.

In another particularly preferred embodiment, the EGFR inhibitor is cetuximab.

Cetuximab is a recombinant, human/mouse chimeric monoclonal antibody that binds specifically to the extracellular domain of the human epidermal growth factor receptor (EGFR). Cetuximab is composed of the Fv regions of a murine anti-EGFR antibody with human IgG1 heavy and kappa light chain constant regions and has an approximate molecular weight of 152 kDa. Cetuximab is produced in mammalian (murine myeloma) cell culture.

Cetuximab has been approved for use as a single agent and in combination with other regimens for the treatment of head and neck and colorectal cancers.

In another particularly preferred embodiment, the EGFR inhibitor is erlotinib. Erlotinib [Tarceva®; N-(3-ethynylphenyl-6,7-bis(2-methoxyethoxy)-4-quinazolin-amine] is a HER1/EGFR inhibitor and has the chemical structure:

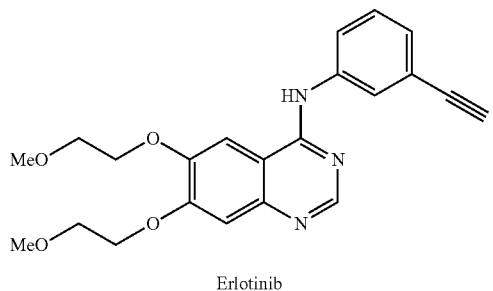 [SMILES: C#Cc1cccc(Nc2ncnc3cc(OCCOC)c(OCCOC)cc23)c1]

Erlotinib

Erlotinib monotherapy has been approved for use for the treatment of patients with locally advanced or metastatic non-small cell lung cancer after the failure of at least one prior chemotherapy regimen.

In another particularly preferred embodiment, the EGFR inhibitor is gefitinib.

Gefitinib [Iressa®; N-(3-chloro-4-fluorophenyl)-7-methoxy-6-[(3,4-morpholin) propoxy]-4-quinazolinamine] has the chemical structure:

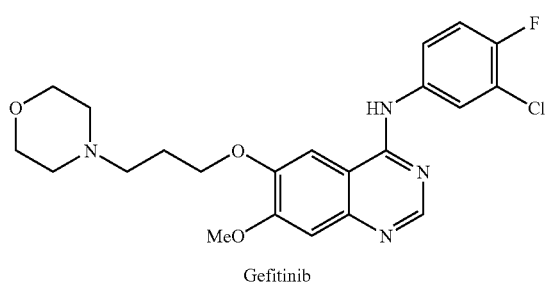 [SMILES: COc1cc2ncnc(Nc3ccc(F)c(Cl)c3)c2cc1OCCCN1CCOCC1]

Gefitinib

Gefitinib has been approved for use as monotherapy for the continued treatment of patients with locally advanced or metastatic non-small cell lung cancer after the failure of both platinum-based and docetaxel chemotherapies.

In one preferred embodiment of the invention, the ErbB inhibitor is lapatinib (Tykerb®). Lapatinib is the compound known as N-[3-chloro-4-[(3-fluorophenyl)methoxy]phenyl]-6-[5-[(2methylsulfonylethylamino)methyl]-2-furyl]quinazolin-4-amine, having the structure shown below:

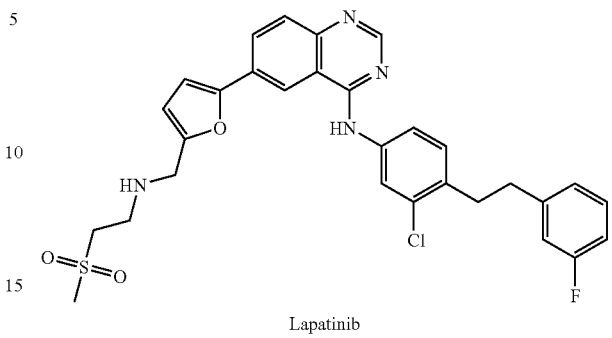

Lapatinib

Lapatinib (INN) or lapatinib ditosylate (USAN), also known as GW572016, is an anti-cancer drug for the treatment of solid tumours such as breast and lung cancer. It has been approved for use in patients with advanced metastatic breast cancer in conjunction with the chemotherapy drug Xeloda. More specifically, lapatinib is a once-daily oral drug indicated for women who have received prior treatment with Herceptin and taxanes and anthracyclines. Lapatinib is an EGFR and HER2/neu (ErbB-2) dual tyrosine kinase inhibitor which binds to the intracellular phosphorylation domain to prevent receptor autophosphorylation upon ligand binding.

In a particularly preferred embodiment, the ErbB inhibitor is selected from AG1478, trastuzumab and erlotinib.

The combinations of the present invention comprise various purine-based CDK inhibitors, for example roscovitine and related compounds of general formula (I).

Preferably, the CDK inhibitor of the presently claimed combination is most potent against CDK2.

More preferably, the CDK inhibitor of the presently claimed combination is most potent against CDK2 and CDK9 with at least 20-fold less activity against CDK1 and CDK4.

Even more preferably, the CDK inhibitor of the presently claimed combination is most potent against CDK2 and CDK9 with at least 50-fold less activity against CDK1 and CDK4.

Even more preferably still, the CDK inhibitor of the presently claimed combination is most potent against CDK2 and CDK9 with at least 100-fold less activity against CDK4.

In one highly preferred embodiment, the CDK inhibitor inhibits CDK2, CDK7 and CDK9 most potently, with at least 20-fold less activity against CDK1 and CDK4.

In one preferred embodiment of the invention, the CDK inhibitor is roscovitine or a pharmaceutically acceptable salt thereof.

Roscovitine or 2-[[(1-ethyl-2-hydroxyethyl)amino]-6-benzylamine-9-isopropylpurine, is also described as 2-(1-D,L-hydroxymethylpropylamino)-6-benzylamine-9-isopropylpurine. As used herein, the term "roscovitine" encompasses the resolved R and S enantiomers, mixtures thereof, and the racemate thereof.

As used herein, the term "seliciclib" refers to the R enantiomer of roscovitine, namely, 2-(1-R-hydroxymethylpropylamino)-6-benzylamino-9-isopropylpurine, the structure of which is shown below.

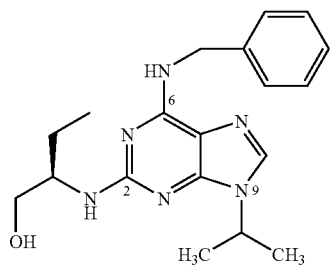 [SMILES: CC[C@H](CO)Nc1nc(NCc2ccccc2)c2ncn(C(C)C)c2n1]

For all embodiments of the invention, preferably roscovitine is in the form of the R enantiomer, namely 2-(1-R-hydroxymethylpropylamino)-6-benzylamino-9-isopropyl-purine, hereinafter referred to as "seliciclib" or "CYC202" or "R-roscovitine".

The in vitro activity of roscovitine is as follows:

| Kinase | IC$_{50}$ (M) |
| --- | --- |
| Cdk1/cyclin B | 2.7 |
| Cdk2/cyclin A | 0.7 |
| Cdk2/cyclin E | 0.1 |
| Cdk7/cyclin H | 0.5 |
| Cdk9/cyclin T1 | 0.8 |
| Cdk4/cyclin D1 | 14.2 |
| PKA | >50 |
| PKC | >50 |

In another highly preferred embodiment, the CDK inhibitor is selected from:

(3R)-3-{9-isopropyl-6-[(pyridin-3-ylmethyl)-amino]-9H-purin-2-ylamino}-2-methyl-pentan-2-ol [1];

(3S)-3-{9-isopropyl-6-[(pyridin-3-ylmethyl)-amino]-9H-purin-2-ylamino}-2-methyl-pentan-2-ol [2];

(2R3S)-3-{9-isopropyl-6-[(pyridin-3-ylmethyl)-amino]-9H-purin-2-ylamino}-pentan-2-ol [3]; and (2R,3S-3-(6-((4,6-dimethylpyridin-3-ylmethylamino)-9-isopropyl-9H-purin-2-ylamino)pentan-2-ol [4].

In another preferred embodiment, the CDK inhibitor is 3-{9-isopropyl-6-[(pyridin-3-ylmethyl)-amino]-9H-purin-2-ylamino}-2-methyl-pentan-2-ol. As used herein, 3-{9-isopropyl-6-[(pyridin-3-ylmethyl)-amino]-9H-purin-2-ylamino}-2-methyl-pentan-2-ol encompasses the resolved R and S enantiomers, mixtures thereof, and the racemate thereof.

In one highly preferred embodiment, the CDK inhibitor is (3R)-3-{9-isopropyl-6-[(pyridin-3-ylmethyl)-amino]-9H-purin-2-ylamino}-2-methyl-pentan-2-ol [1], the structure of which is shown below:

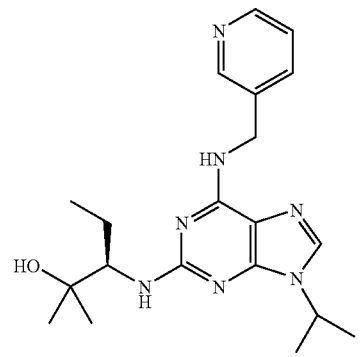

In another highly preferred embodiment, the CDK inhibitor is (3S)-3-{9-isopropyl-6-[(pyridin-3-ylmethyl)-amino]-9H-purin-2-ylamino}-2-methyl-pentan-2-ol [2], the structure of which is shown below:

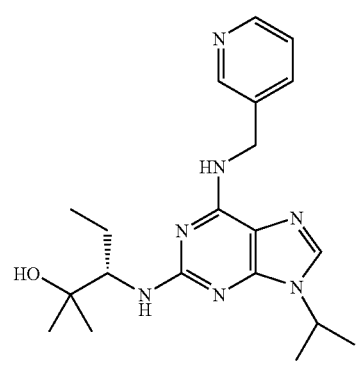

In yet another preferred embodiment, the CDK inhibitor is 3-{9-isopropyl-6-[(pyridin-3-ylmethyl)-amino]-9H-purin-2-ylamino}-pentan-2-ol. As used herein, 3-{9-isopropyl-6-[(pyridin-3-ylmethyl)-amino]-9H-purin-2-ylamino}-pentan-2-ol encompasses the resolved, as well as the unresolved diastereoisomers, and mixtures thereof.

In a highly preferred embodiment, the CDK inhibitor is (2R3S)-3-{9-isopropyl-6-[(pyridine-3-ylmethyl)-amino]-9H-purin-2-ylamino}-pentan-2-ol [3], the structure of which is shown below:

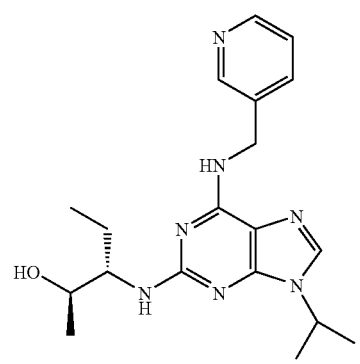

In yet another preferred embodiment, the CDK inhibitor is (2R,3S-3-(6-((4,6-dimethylpyridin-3-ylmethylamino)-9-isopropyl-9H-purin-2-ylamino)pentan-2-ol [4], the structure of which is shown below:

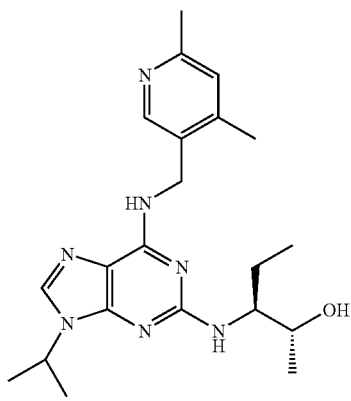

[4]

Another aspect relates to a pharmaceutical composition comprising a combination according to the invention and a pharmaceutically acceptable carrier, diluent or excipient.

Another aspect relates to a pharmaceutical product comprising the combination of the present invention for use in the treatment of a proliferative disorder.

Many anti-cancer agents are given in combination in order to optimise the treatment regime. The effect of drug combinations is inherently unpredictable and there is often a propensity for one drug to partially or completely inhibit the effects of the other.

The present invention is based on the surprising observation that administering a combination comprising an ErbB inhibitor (for example, an EGFR inhibitor), or a pharmaceutically acceptable salt thereof, and a CDK inhibitor, either simultaneously, separately or sequentially, does not lead to any significant or dramatic adverse interaction between the two agents. The unexpected absence of any such antagonistic interaction is critical for clinical applications.

Preferably, the combination of the invention is a synergistic combination comprising an ErbB inhibitor (for example, an EGFR inhibitor), and a CDK inhibitor as defined above, or a pharmaceutically acceptable salt thereof, i.e. the combination has a synergistic effect.

In a preferred embodiment, the combination of the ErbB inhibitor and the CDK inhibitor, or pharmaceutically acceptable salt thereof, produces an enhanced effect as compared to either drug administered alone. The surprising nature of this observation is in contrast to that expected on the basis of the prior art. Advantageously, a synergistic interaction may allow for lower doses of each component to be administered to a patient, thereby decreasing the toxicity of chemotherapy, whilst producing and/or maintaining the same therapeutic effect. Thus, in a particularly preferred embodiment, each component can be administered in a sub-therapeutic amount.

In another preferred embodiment, the ErbB inhibitor and the CDK inhibitor, or pharmaceutically acceptable salt thereof, interact in a manner so as to alleviate or eliminate adverse side effects associated with the use of the individual components in monotherapy, or associated with their use in known combinations.

As mentioned above, one aspect of the invention relates to a pharmaceutical product comprising an ErbB inhibitor and a CDK inhibitor, or a pharmaceutically acceptable salt thereof, selected from: (a) roscovitine; (b) 3-{9-isopropyl-6-[(pyridin-3-ylmethyl)-amino]-9H-purin-2-ylamino}-2-methyl-pentan-2-ol; (c) 3-{9-isopropyl-6-[(pyridin-3-ylmethyl)-amino]-9H-purin-2-ylamino}-pentan-2-ol; and (d) (2R,3S-3-(6-((4,6-dimethylpyridin-3-ylmethylamino)-9-isopropyl-9H-purin-2-ylamino)pentan-2-ol as a combined preparation for simultaneous, sequential or separate use in therapy.

The combination comprising the ErbB inhibitor and the CDK inhibitor, or pharmaceutically acceptable salt thereof, may be administered simultaneously, sequentially or separately (as part of a dosing regime).

As used herein, "simultaneously" is used to mean that the two agents are administered concurrently. Thus, administration "sequentially" may permit one agent to be administered within 5 minutes, 10 minutes or a matter of hours after the other provided the circulatory half-life of the first administered agent is such that they are both concurrently present in therapeutically effective amounts. The time delay between administration of the components will vary depending on the exact nature of the components, the interaction therebetween, and their respective half-lives.

In contrast to "sequentially", "separately" is used herein to mean that the gap between administering one agent and the other is significant i.e. the first administered agent may no longer be present in the bloodstream in a therapeutically effective amount when the second agent is administered.

In one preferred embodiment, the second agent is administered at least 2 hours, more preferably at least 4 hours, even more preferably at least 8 hours, even more preferably still at least 12 or 24 or 48 or 72 hours after the first agent. In one particularly preferred embodiment, the second agent is administered at least 24 hours after the first agent.

In one aspect, the present invention relates to a method of treating a proliferative disorder, said method comprising simultaneously, sequentially or separately administering to a subject an ErbB inhibitor and a CDK inhibitor, or a pharmaceutically acceptable salt thereof, selected from: (a) roscovitine; (b) 3-{9-isopropyl-6-[(pyridin-3-ylmethyl)-amino]-9H-purin-2-ylamino}-2-methyl-pentan-2-ol; (c) 3-{9-isopropyl-6-[(pyridin-3-ylmethyl)-amino]-9H-purin-2-ylamino}-pentan-2-ol; and (d) (2R,3S-3-(6-((4,6-dimethylpyridin-3-ylmethylamino)-9-isopropyl-9H-purin-2-ylamino)pentan-2-ol.

Preferably, the subject is a mammal, more preferably a human.

In one preferred embodiment, the ErbB inhibitor and the CDK inhibitor, or pharmaceutically acceptable salt, are administered simultaneously.

In another preferred embodiment, the ErbB inhibitor and the CDK inhibitor, or pharmaceutically acceptable salt thereof, are administered sequentially or separately.

Preferably, the ErbB inhibitor is administered at least 2 hours, more preferably at least 4 hours, even more preferably at least 8 hours, even more preferably still at least 12 or 24 or 48 or 72 hours before the CDK inhibitor, or pharmaceutically acceptable salt thereof. In one particularly preferred embodiment, the ErbB inhibitor is administered at least 24 hours before the CDK inhibitor, or pharmaceutically acceptable salt thereof. In another preferred embodiment, the ErbB inhibitor and the CDK inhibitor, or pharmaceutically acceptable salt thereof, are each administered in a therapeutically effective amount with respect to the individual components.

In an alternative preferred embodiment, the ErbB inhibitor and the CDK inhibitor, or pharmaceutically acceptable salt thereof, are each administered in a sub-therapeutically effective amount with respect to the individual components.

The term "sub-therapeutically effective amount" means an amount that is lower than that typically required to produce a therapeutic effect with respect to treatment with the ErbB inhibitor or the CDK inhibitor, or pharmaceutically acceptable salt thereof, alone.

In a highly preferred embodiment, the ErbB inhibitor is administered sequentially or separately prior to the CDK inhibitor, or pharmaceutically acceptable salt thereof.

In another highly preferred embodiment, the CDK inhibitor, or pharmaceutically acceptable salt thereof, is administered sequentially or separately prior to the ErbB inhibitor.

Proliferative Disorder

The term "proliferative disorder" is used herein in a broad sense to include any disorder that requires control of the cell cycle, for example cardiovascular disorders such as restenosis and cardiomyopathy, auto-immune disorders such as glomerulonephritis, lupus nephritis, mesangial proliferative disorders and rheumatoid arthritis, cystic diseases such as polycystic kidney disease, polycystic liver disease, medullary cystic disease, dermatological disorders such as psoriasis, anti-inflammatory, anti-fungal, antiparasitic disorders such as malaria, emphysema and alopecia. In these disorders, the compounds of the present invention may induce apoptosis or maintain stasis within the desired cells as required.

In respect of all of the above aspects and embodiments, preferably the proliferative disorder is cancer.

In one highly preferred embodiment, the proliferative disorder is ovarian cancer.

In yet another highly preferred embodiment, the proliferative disorder is head or neck cancer.

In yet another highly preferred embodiment, the proliferative disorder is breast cancer.

In yet another highly preferred embodiment, the proliferative disorder is lung cancer, more preferably, NSCLC.

In one preferred embodiment, the present invention relates to a method of treating non-small cell lung cancer, said method comprising simultaneously, sequentially or separately administering to a subject an ErbB inhibitor and a CDK inhibitor, or a pharmaceutically acceptable salt thereof, selected from: (a) roscovitine; (b) 3-{9-isopropyl-6-[(pyridin-3-ylmethyl)-amino]-9H-purin-2-ylamino}-2-methyl-pentan-2-ol; (c) 3-{9-isopropyl-6-[(pyridin-3-ylmethyl)-amino]-9H-purin-2-ylamino}-pentan-2-ol; and (d) (2R,3S-3-(6-((4,6-dimethylpyridin-3-ylmethylamino)-9-isopropyl-9H-purin-2-ylamino)pentan-2-ol.

Lung cancers (bronchogenic carcinomas) may be divided into two broad categories namely, small cell lung cancer (SCLC) and non-small cell lung cancer (NSCLC). The distinction between these two types of cancer is based on the appearance of the tumour cells when viewed under a microscope.

SCLC accounts for 20% of lung cancers diagnosed and is characterised by small cells which are mostly filled with the nucleus (hence the name). It is sometimes also referred to as "oat cell" cancer. SCLC is the most aggressive type of cancer, which metastasizes rapidly to other parts of the body. Diagnosis with SCLC often occurs only after the cancer has spread throughout the body. In general, SCLC is almost always caused as a result of smoking.

NSCLC can be subdivided into a group of related lung cancers which include epidermoid or squamous cell carcinoma, adenocarcinoma and large cell carcinoma.

Squamous cell lung cancer accounts for approximately 30% of all lung cancer cases and develops from reserve cells (which have the role of replacing damaged epithelium cells) in the lining of the lungs and bronchi. As a result, the cancer often initially develops in the centre of the chest. Squamous cell lung cancers are frequently slow growing and can take several years to progress from a confined tumour into invasive cancer. In 10-20% of cases, the cancer cavitates within the lungs. On metastasis, it often spreads to the bone, liver, adrenal glands, small intestine and brain.

Adenocarcinoma is the most common form of lung cancer making up 30-40% of all lung cancer cases. Adenocarcinoma develops in the outer part of the lung and develops from mucus-producing cells. The course of this cancer varies widely but often progresses slowly and the patient will present with few or no symptoms. In some cases, however, it can be extremely aggressive and rapidly fatal. In 50% of cases when it metastasises, it spreads only to the brain. Other locations to which adenocarcinoma spreads include the liver, the adrenal glands and bone.

The incidence of large cell carcinoma occurs less frequently than that of either adenocarcinoma or squamous cell carcinoma and accounts for 10-20% of lung cancer cases. The cancer is composed of large-sized cells that are anaplastic in nature and often arise in the bronchi. Large cell carcinoma develops on the periphery of the lungs and can spread to the plura.

Currently, lung cancer may be treated by surgery, radiation therapy or chemotherapy. Chemotherapy may be administered either alone or in combination with the other treatment options. Common NSCLC drugs and regimens include Camptosar® (irinotecan; CPT-11), camptothecin, Paraplatin® (carboplatin), Platinol® (cisplatin), epirubicin, Gemzar® (gemcitabine), Navelbine® (vinorelbine), oxaliplatin, Taxol® (paclitaxel) and Taxotere® (docetaxol) (NSCLC Treatment—Chemotherapy, Lung Cancer Online).

However, chemotherapy is not curative. Other disadvantages of this treatment include toxicity, bystander damage to normal tissues and drug resistance (W. Wang et al, Cancer Sci., 2005, 96(10), 706). Furthermore, studies have shown that there is little survival benefit with some of the known treatments, such as vinorelbine (M. A. Socinski et al, Clin. Adv. Hematol. Oncol., 2003, 1(1), 33). Even a novel active such as troxacitabine has been shown to have little activity in NSCLC in 10 mg/m² doses administered intravenously over 30 minutes every three weeks (S. F. Dent et al, Lung, 2005, 183(4), 265).

The combination of gemcitabine/cisplatin has become widely used in Europe for the treatment of NSCLC. Cisplatin, however, is acknowledged to have certain disadvantages in that significant non-hematological toxicity (ototoxicity and nephrotoxicity) occurs in patients, along with emesis (P. Zatloukal et al, Lung Cancer, 2002, 38, S33).

As the outcome for a patient diagnosed with lung cancer is poor—the ten year survival rate for all treated cases is only approximately 8%—there exists a continuing need to develop effective treatments.

In one highly preferred embodiment, the EGFR inhibitor is erlotinib and the CDK inhibitor is seliciclib. Preferably, the proliferative disorder is lung cancer, more preferably, non small cell lung cancer.

In another highly preferred embodiment, the EGFR inhibitor is erlotinib and the CDK inhibitor is selected from:
(3R)-3-{9-isopropyl-6-[(pyridin-3-ylmethyl)-amino]-9H-purin-2-ylamino}-2-methyl-pentan-2-ol;
(3S)-3-{9-isopropyl-6-[(pyridin-3-ylmethyl)-amino]-9H-purin-2-ylamino}-2-methyl-pentan-2-ol;
(2R3S)-3-{9-isopropyl-6-[(pyridin-3-ylmethyl)-amino]-9H-purin-2-ylamino}-pentan-2-ol; and
(2R,3S-3-(6-((4,6-dimethylpyridin-3-ylmethylamino)-9-isopropyl-9H-purin-2-ylamino)pentan-2-ol.

In one particularly preferred embodiment, the EGFR inhibitor is AG1478 and the CDK inhibitor is seliciclib. Preferably, the proliferative disorder is lung cancer, more preferably, non small cell lung cancer.

In yet another particularly preferred embodiment, the EGFR inhibitor is AG1478 and the CDK inhibitor is (3R)-3-{9-isopropyl-6-[(pyridin-3-ylmethyl)-amino]-9H-purin-2-ylamino}-2-methyl-pentan-2-ol. Preferably, the proliferative disorder is lung cancer or breast cancer.

In another particularly preferred embodiment, the EGFR inhibitor is AG1478 and the CDK inhibitor is (3S)-3-{9-isopropyl-6-[(pyridin-3-ylmethyl)-amino]-9H-purin-2-ylamino}-2-methyl-pentan-2-ol. Preferably, the proliferative disorder is lung cancer or breast cancer.

In yet another particularly preferred embodiment, the EGFR inhibitor is AG1478 and the CDK inhibitor is (2R3S)-3-{9-isopropyl-6-[(pyridin-3-ylmethyl)-amino]-9H-purin-2-ylamino}-pentan-2-ol. Preferably, the proliferative disorder is lung cancer or breast cancer.

In a particularly preferred embodiment, the ErbB inhibitor is trastuzumab and the CDK inhibitor is seliciclib. Preferably, the proliferative disorder is breast cancer.

In a particularly preferred embodiment, the EGFR inhibitor is lapatinib and the CDK inhibitor is seliciclib. Preferably, the proliferative disorder is breast cancer.

In a particularly preferred embodiment, the EGFR inhibitor is lapatinib and the CDK inhibitor is (3R)-3-{9-isopropyl-6-[(pyridin-3-ylmethyl)-amino]-9H-purin-2-ylamino}-2-methyl-pentan-2-ol. Preferably, the proliferative disorder is breast cancer.

In one particularly preferred embodiment, the EGFR inhibitor is selected from erlotinib, gefitinib, AG1478 and lapatinib, and the CDK inhibitor is seliciclib. Preferably, the proliferative disorder is breast cancer or lung cancer.

In one particularly preferred embodiment, the EGFR inhibitor is selected from erlotinib, gefitinib, AG1478 and lapatinib, and the CDK inhibitor is (3R)-3-{9-isopropyl-6-[(pyridin-3-ylmethyl)-amino]-9H-purin-2-ylamino}-2-methyl-pentan-2-ol. Preferably, the proliferative disorder is breast cancer or lung cancer.

In one particularly preferred embodiment, the EGFR inhibitor is selected from erlotinib, gefitinib, AG1478 and lapatinib, and the CDK inhibitor is (3S)-3-{9-isopropyl-6-[(pyridin-3-ylmethyl)-amino]-9H-purin-2-ylamino}-2-methyl-pentan-2-ol. Preferably, the proliferative disorder is breast cancer or lung cancer.

In one particularly preferred embodiment, the EGFR inhibitor is selected from erlotinib, gefitinib, AG1478 and lapatinib, and the CDK inhibitor is (2R3S)-3-{9-isopropyl-6-[(pyridin-3-ylmethyl)-amino]-9H-purin-2-ylamino}-pentan-2-ol. Preferably, the proliferative disorder is breast cancer or lung cancer.

In one particularly preferred embodiment, the EGFR inhibitor is selected from erlotinib, gefitinib, AG1478 and lapatinib, and the CDK inhibitor is (2R,3S-3-(6-((4,6-dimethylpyridin-3-ylmethylamino)-9-isopropyl-9H-purin-2-ylamino)pentan-2-ol. Preferably, the proliferative disorder is breast cancer or lung cancer.

In one particularly preferred embodiment, the EGFR inhibitor is erlotinib and the CDK inhibitor is (3R)-3-{9-isopropyl-6-[(pyridin-3-ylmethyl)-amino]-9H-purin-2-ylamino}-2-methyl-pentan-2-ol. Preferably, the proliferative disorder is lung cancer.

In one highly preferred embodiment, the invention relates to a method of treating lung cancer comprising administering to a subject a combination comprising erlotinib and seliciclib.

In another highly preferred embodiment, the invention relates to a method of treating breast cancer comprising administering to a subject a combination comprising erlotinib and seliciclib.

In another highly preferred embodiment, the invention relates to a method of treating lung cancer comprising administering to a subject a combination comprising trastuzumab and seliciclib. Preferably, the agents of the combination are administered concomitantly.

In another highly preferred embodiment, the invention relates to a method of treating breast cancer comprising administering to a subject a combination comprising trastuzumab and seliciclib. Preferably, the agents of the combination are administered concomitantly.

In another highly preferred embodiment, the invention relates to a method of treating lung cancer comprising administering to a subject a combination comprising AG1478 and seliciclib. Preferably, the agents of the combination are administered concomitantly.

Combinations Comprising Compounds of Formula (I)

One aspect of the invention relates to a combination comprising (i) an ErbB inhibitor; and (ii) a compound of formula I, or a pharmaceutically acceptable salt thereof,

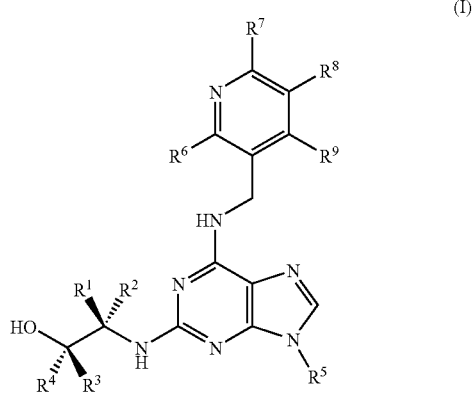

(I)

wherein:
$R^1$ and $R^2$ are each independently H or alkyl;
$R^3$ and $R^4$ are each independently H, alkyl or aryl;
$R^5$ is alkyl or cycloalkyl, each of which may be optionally substituted with one or more OH groups;
$R^6$, $R^7$, $R^8$ and $R^9$ are each independently H, alkyl, haloalkyl, halogen, $NO_2$, OH, OMe, CN, $NH_2$, COOH, $CONH_2$, or $SO_2NH_2$.

As used herein, the term "alkyl" includes both saturated straight chain and branched alkyl groups. Preferably, the alkyl group is a $C_{1-20}$ alkyl group, more preferably a $C_{1-15}$, more preferably still a $C_{1-12}$ alkyl group, more preferably still, a $C_{1-6}$ alkyl group, more preferably a $C_{1-3}$ alkyl group. Particularly preferred alkyl groups include, for example, methyl, ethyl, propyl, isopropyl, butyl, isobutyl, tert-butyl, pentyl and hexyl.

As used herein, the term "cycloalkyl" refers to a cyclic alkyl group. Preferably, the cycloalkyl group is a $C_{3-12}$ cycloalkyl group.

As used herein, the term "aryl" refers to a $C_{6-12}$ aromatic group. Typical examples include phenyl and naphthyl etc.

Preferably, for this aspect of the invention, at least one of $R^3$ and $R^4$ is other than H.

In one preferred embodiment, $R^3$ and $R^4$ are each independently H, methyl, ethyl, n-propyl, isopropyl, n-butyl, s-butyl, t-butyl or phenyl.

More preferably, $R^3$ and $R^4$ are each independently H, methyl, ethyl, n-propyl, isopropyl, n-butyl, s-butyl or t-butyl.

Even more preferably, $R^3$ and $R^4$ are each independently H, methyl, ethyl, isopropyl or t-butyl.

In one preferred embodiment, $R^6$, $R^7$, $R^8$ and $R^9$ are each independently H, alkyl or haloalkyl. More preferably, $R^6$, $R^7$, $R^8$ and $R^9$ are each independently H or alkyl. In one especially preferred embodiment, $R^6$, $R^7$, $R^8$ and $R^9$ are all H. In another especially preferred embodiment, $R^6$ and $R^8$ are H and $R^7$ and $R^9$ are Me.

In one preferred embodiment, one of $R^1$ and $R^2$ is ethyl or isopropyl, and the other is H. More preferably, one of $R^1$ and $R^2$ is ethyl and the other is H.

In one preferred embodiment, $R^5$ is isopropyl or cyclopentyl.

In one highly preferred embodiment of the invention, the compound of formula (I) is selected from:
3-{9-isopropyl-6-[(pyridin-3-ylmethyl)-amino]-9H-purin-2-ylamino}-2-methyl-pentan-2-ol;
3-{9-isopropyl-6-[(pyridin-3-ylmethyl)-amino]-9H-purin-2-ylamino}-pentan-2-ol;
(2R,3S-3-(6-((4,6-dimethylpyridin-3-ylmethylamino)-9-isopropyl-9H-purin-2-ylamino)pentan-2-ol;
(3R)-3-{9-isopropyl-6-[(pyridin-3-ylmethyl)-amino]-9H-purin-2-ylamino}-2-methyl-pentan-2-ol; and
(3S)-3-{9-isopropyl-6-[(pyridin-3-ylmethyl)-amino]-9H-purin-2-ylamino}-2-methyl-pentan-2-ol.

Pharmaceutical Compositions

In a particularly preferred embodiment, the pharmaceutical product of the invention is in the form of a pharmaceutical composition comprising a pharmaceutically acceptable carrier, diluent or excipient.

Even though the compounds of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients", $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Prodrugs

The invention further includes agents of the present invention in prodrug form. Such prodrugs are generally compounds wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include esters (for example, any of those described above), wherein the reversion may be carried out be an esterase etc. Other such systems will be well known to those skilled in the art.

Salts/Esters

The agents of the present invention can be present as salts or esters, in particular pharmaceutically acceptable salts or esters.

Pharmaceutically acceptable salts of the agents of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as (C1-C4)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as (C1-C4)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminum hydroxide. Alcohols include alkanealcohols of 1-12 carbon atoms which may be unsubstituted or substituted, e.g. by a halogen).

Enantiomers/Tautomers

The invention also includes where appropriate all enantiomers and tautomers of the agents. The man skilled in the art will recognise compounds that possess optical properties (one or more chiral carbon atoms) or tautomeric characteristics. The corresponding enantiomers and/or tautomers may be isolated/prepared by methods known in the art.

Stereo and Geometric Isomers

Some of the agents of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or pharmaceutically acceptable salts thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as 2H, 3H, 13C, 14C, 15N, 17O, 18O, 31P, 32P, 35S, 18F and 36Cl, respectively. Certain isotopic variations of the agent and pharmaceutically acceptable salts thereof, for example, those in which a radioactive isotope such as 3H or 14C is incorporated, are useful in drug and/or substrate tissue distribution studies. Tritiated, i.e., 3H, and carbon-14, i.e., 14C, isotopes are particularly preferred for their ease of preparation and detectability. Further, substitution with isotopes such as deuterium, i.e., 2H, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes solvate forms of the agents of the present invention. The terms used in the claims encompass these forms.

Polymorphs

The invention furthermore relates to agents of the present invention in their various crystalline forms, polymorphic forms and (an)hydrous forms. It is well established within the pharmaceutical industry that chemical compounds may be isolated in any of such forms by slightly varying the method of purification and or isolation from the solvents used in the synthetic preparation of such compounds.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 2000 mg and more preferably from 50-1000 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-500 mg, of active ingredient per dose.

Compositions may be formulated in unit dosage form, i.e., in the form of discrete portions containing a unit dose, or a multiple or sub-unit of a unit dose.

In one preferred embodiment, the CDK inhibitor, or pharmaceutically acceptable salt thereof, is administered orally or intravenously.

In one preferred embodiment, AG1478 is administered intravenously.

In one preferred embodiment, trastuzumab is administered intravenously.

In one preferred embodiment, cetuximab is administered intravenously.

In one preferred embodiment, erlotinib is administered orally.

In one preferred embodiment, gefitinib is administered orally.

In one preferred embodiment, lapatinib is administered orally.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the agent may be administered at a dose of from 0.1 to 30 mg/kg body weight, such as from 0.1 to 10 mg/kg, more preferably from 2 to 20 mg/kg body weight.

The CDK inhibitor, or pharmaceutically acceptable salt thereof, is typically administered from about 0.05 to about 5 g/day, preferably from about 0.4 to about 3 g/day. Roscovitine is preferably administered orally in tablets or capsules. The total daily dose of roscovitine can be administered as a single dose or divided into separate dosages administered two, three or four times a day.

Preferably, roscovitine is administered orally or intravenously at a dosage of from 0.4 to 3 g/day.

By way of guidance, the ErbB inhibitor is typically administered in accordance with a physician's direction at dosages described in the relevant references or between the approved dosages for said ErbB inhibitor. Said approved dosages are available from the Summary of Product Characteristics for each agent which may be obtained from the manufacturer or from the literature e.g. www.emea.eu.int/htms/human/epar/a-zepar.htm.

Kit of Parts

A further aspect of the invention relates to a kit of parts comprising:
(i) an ErbB inhibitor; and
(ii) a CDK inhibitor, or a pharmaceutically acceptable salt thereof, selected from: (a) roscovitine; (b) 3-{9-isopropyl-6-[(pyridin-3-ylmethyl)-amino]-9H-purin-2-ylamino}-2-methyl-pentan-2-ol; (c) 3-{9-isopropyl-6-[(pyridin-3-ylmethyl)-amino]-9H-purin-2-ylamino}-pentan-2-ol; and
(d) (2R,3S-3-(6-((4,6-dimethylpyridin-3-ylmethylamino)-9-isopropyl-9H-purin-2-ylamino)pentan-2-ol.

Preferably, the ErbB inhibitor and the CDK inhibitor, or pharmaceutically acceptable salt thereof, are each in unit dosage form. Preferably, the kit of parts contains a plurality of unit dosage forms of each component, i.e. of components (i) and (ii) above. Optionally, the kit of parts may further comprise a means for facilitating compliance with a particular dosing regimen, for example, instructions indicating when, how, and how frequently the unit dosage forms of each component should be taken.

The present invention is further described by way of example, and with reference to the following figures, wherein:

FIG. 1 shows that seliciclib and trastuzumab synergistically downregulate HER2 levels in SkBr3 cells. In more detail, SkBr3 cells were seeded at approximately $8 \times 10^5$ cells/plate in 10 cm dishes and left to settle overnight. Cells were incubated with the indicated concentration of trastuzumab (A), seliciclib (B) or seliciclib+trastuzumab (C) for 24 h prior to harvesting. Protein lysates (30 μg) from each treatment were resolved on 3-8% acrylamide Tris-acetate gels or 10% acrylamide Bis-Tris gels, transferred to nitrocellulose membranes and probed with the antibodies shown. Results are representative of two independent experiments.

FIG. 2 shows the analysis of EGFR signalling pathway proteins in A549, H460 and H358 cell lysates. In more detail, lysates (30 μg) from untreated A549, H460 and H358 cells were resolved on 3-8% acrylamide Tris-acetate gels or 10% acrylamide Bis-Tris gels, transferred to nitrocellulose membranes and probed with the antibodies shown. Results are representative of two independent experiments.

Figure 3:
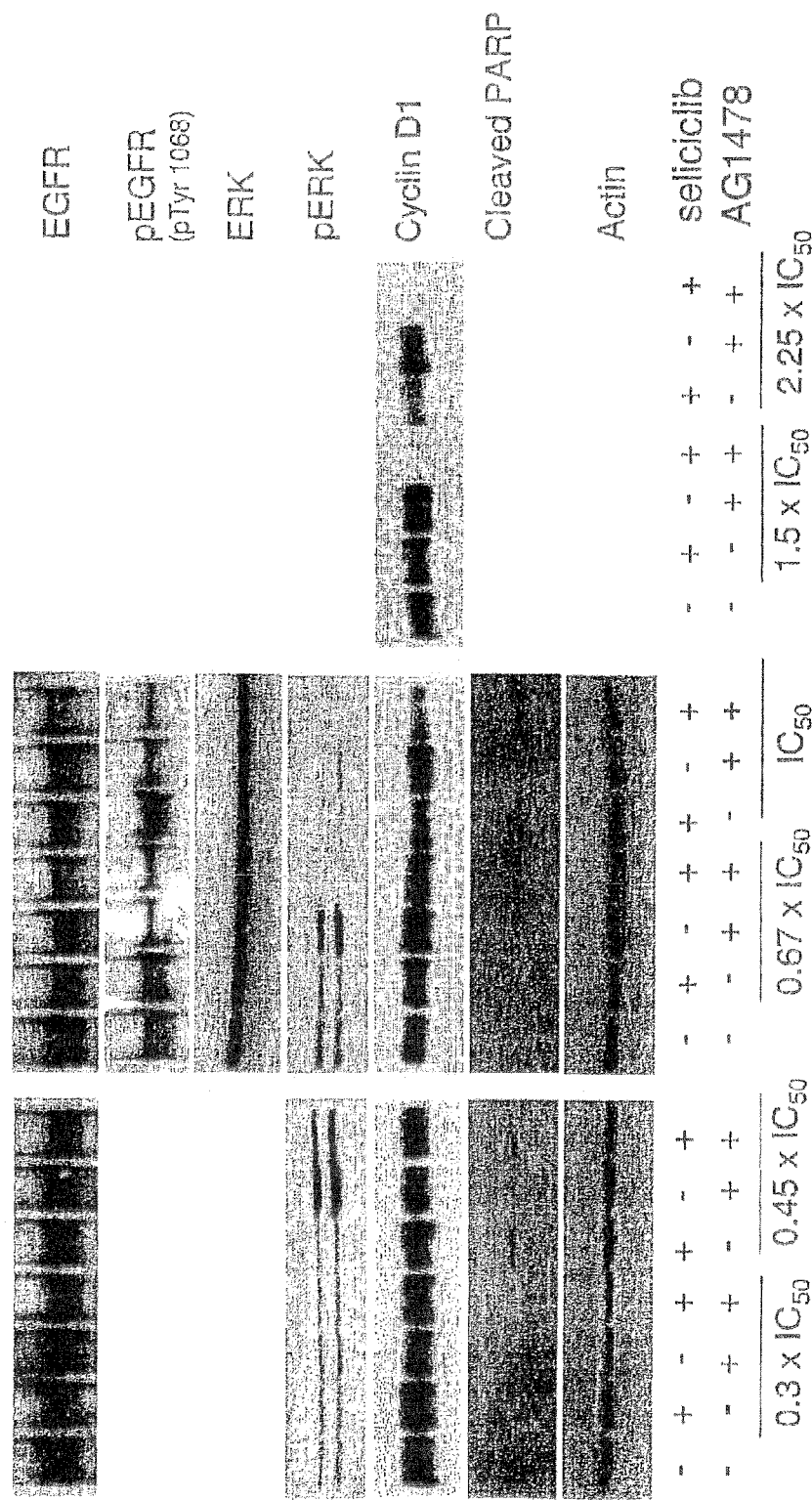

FIG. 3 shows seliciclib and AG1478 synergistically downregulate EGFR signalling in H358 cells. In more detail, H358 cells were seeded at approximately $8 \times 10^5$ cells/plate in 10 cm dishes and left to settle overnight. Cells were incubated in the presence (+) or absence (−) of seliciclib and AG1478, for 72 h prior to harvesting. In H358 cells the $IC_{50}$ for seliciclib was 8.5 μM and for AG1478 it was 4.0 μM. Protein lysates (30 μg) from each treatment were resolved on 3-8% acrylamide Tris-acetate gels or 10% acrylamide Bis-Tris gels, transferred to nitrocellulose membranes and probed with the antibodies shown. Results are representative of two independent experiments.

Figure 4:
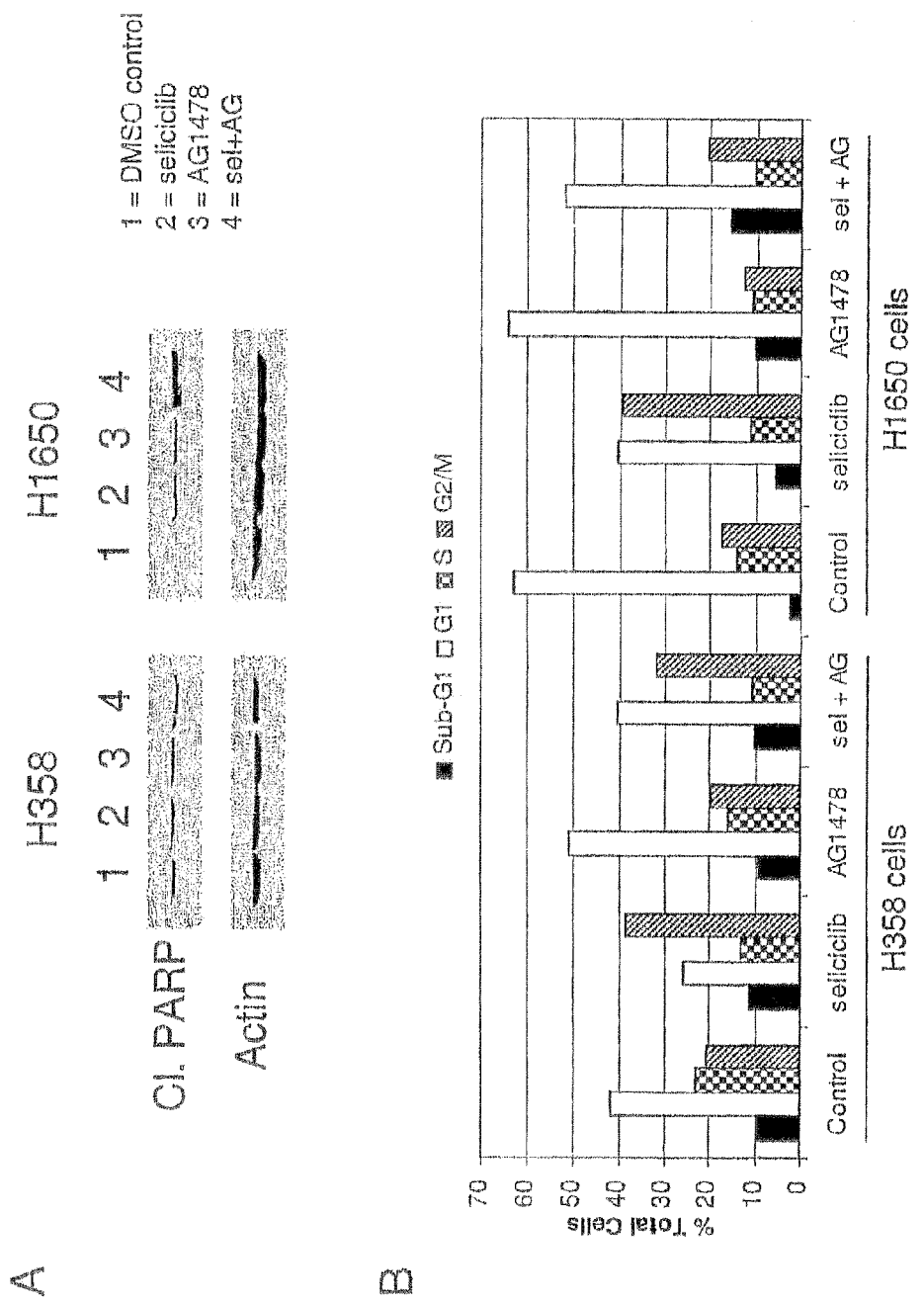

FIG. 4 shows that seliciclib and AG1478 induce increased apoptosis in a cell line dependent manner. In more detail, H358 cells or H1650 cells were treated with $1 \times IC_{50}$ seliciclib, AG1478, or seliciclib and AG1478 for 72 h prior to harvesting and analysis for markers of apoptosis. (A) Protein lysates (25 μg) from each treatment were resolved on 4-12% acrylamide Bis-Tris gels, transferred to nitrocellulose membranes and probed with antibodies that recognise cleaved PARP and actin (as a loading control). (B) The DNA content of the cells was analysed by flow cytometry after propidium iodide staining. Sub-G1 cells are those that contain less DNA than normal diploid cells. Results are representative of two independent experiments.

Figure 5:
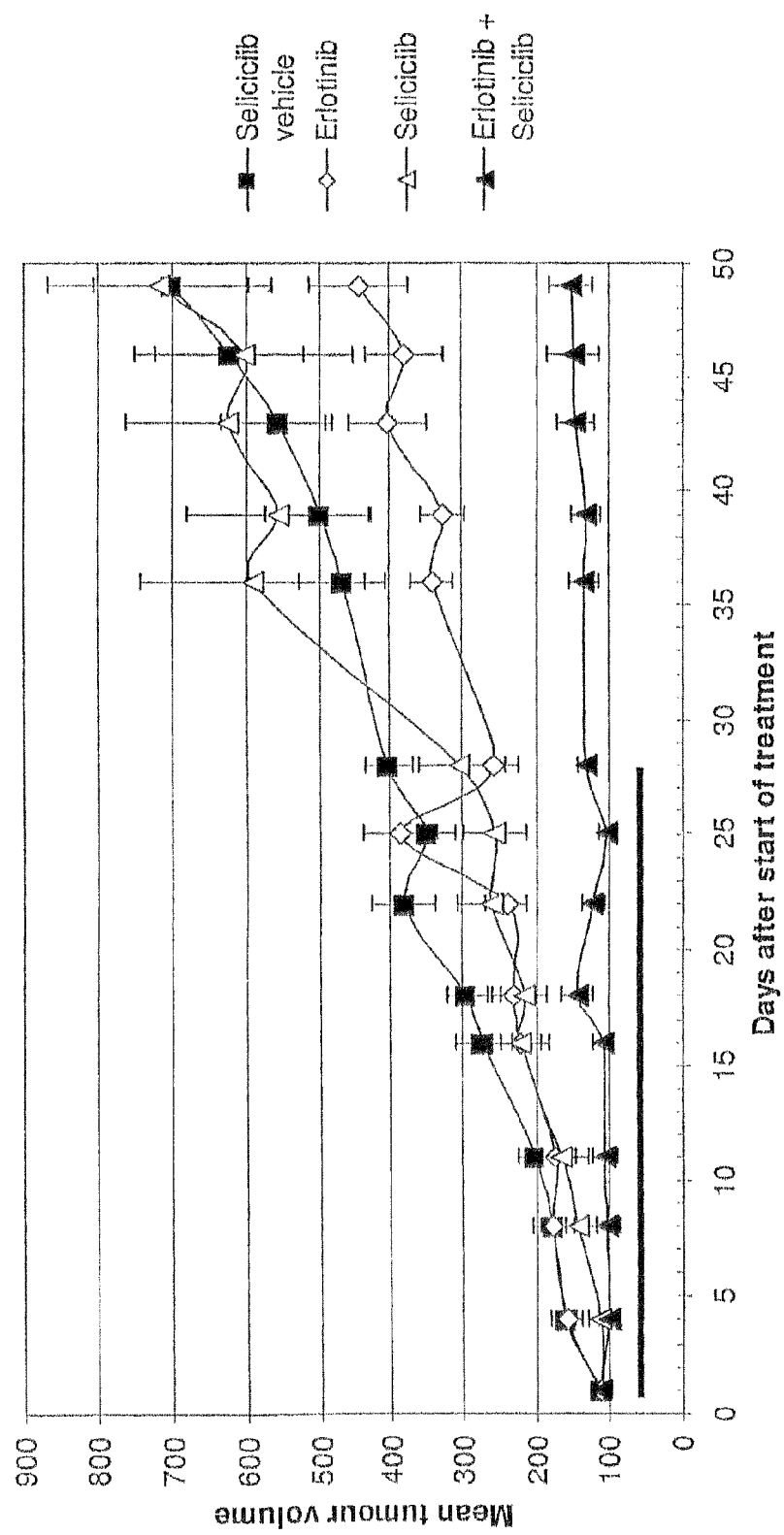

FIG. 5 shows the effect of the combination of seliciclib and erlotinib on the growth of an H358 xenograft. In more detail, mice (nu/nu) were injected subcutaneously with $\sim 1 \times 10^7$ H358 cells/mouse at a single site on their flanks. Treatment was initiated when tumours were $\sim 110$ mm$^3$ and continued for 28 days. Results show mean tumour volume (±SEM) for each treatment group (9 mice/group) and represent treatment with vehicle, seliciclib (50 mg/kg) as a twice daily intraperitoneal injection for five consecutive days followed by a two day break and then repeated for a total of four cycles, erlotinib (100 mg/kg) daily by oral gavage for 28 consecutive days, or the combination of both agents.

Figure 6:
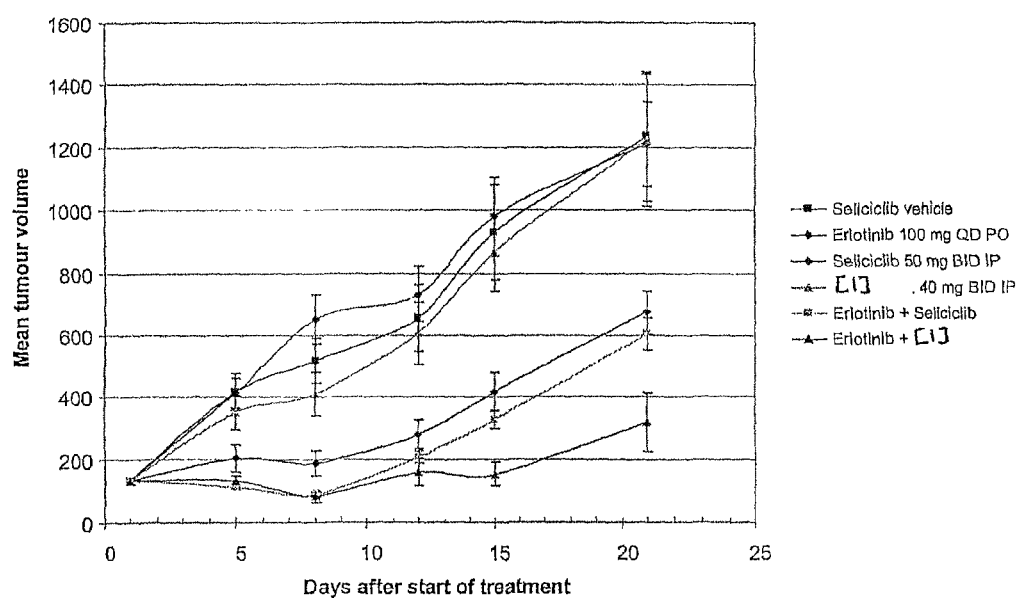

FIG. 6 shows the effect of seliciclib (50 mg BID IP), compound [1] (40 mg BID IP), erlotinib (100 mg QD PO) and combinations of erlotinib+seliciclib, and erlotinib+compound [1], on mean tumour volume using an H292 xenograft model.

EXAMPLES

Materials and Methods
General

Chemicals and solvents were purchased from commercial sources and were used as received unless otherwise stated. THF and Et$_2$O were dried by heating under reflux with sodium-benzophenone under N$_2$ and collected by distillation. Toluene was dried by heating under reflux over sodium under N$_2$. CH$_2$Cl$_2$ was dried by heating under reflux over CaH$_2$ under N$_2$. The microwave generator used was a CEM "Discover" model, with a circular single mode cavity design, that focuses the microwave radiation on the sample tube. TLC (thin-layer chromatography) was performed using glass plates coated with silica gel G60 (0.25 cm). Developed plates were air dried and analysed under a UV lamp (254/365 nm). Anhydrous MgSO$_4$ was used as a standard drying agent for organic solutions unless otherwise stated. Flash column chromatography was performed using Fluorochem silica gel (35-70 μm). Melting points (mp) were determined with an Electrothermal 9100 capillary melting point apparatus and are uncorrected. The abbreviation (dec) denotes a decomposition point. $^1$H-NMR spectra were recorded on a Bruker Avance 300 (300.1 MHz) or a Varian Gemini 2000 (300 MHz) spectrometer using the deuterated solvent as the lock and the residual solvent as the internal reference in all cases. $^{13}$C-NMR spectra using the PENDANT sequence were recorded on a Bruker Avance 300 (75.5 MHz) spectrometer. All other $^{13}$C-spectra were recorded on a Varian Gemini 2000 (75.5 MHz) spectrometer using composite pulse $^1$H decoupling. Coupling constants (J) are quoted to the nearest 0.1 Hz. The following abbreviations are used: s, singlet; d, doublet; t, triplet; q, quartet; qu, quintuplet; m, multiplet and br, broad. Elemental microanalyses were performed by Mrs S Williamson, School of Chemistry, Purdie Building, University of St. Andrews, UK. Results obtained were within 0.4% of calculated values. Electrospray mass spectra (ESI) were recorded on a Micromass LCT mass spectrometer, coupled to a Waters 2975 HPLC. Analytical RP-HPLC was performed using a Dionex ASI-100 automated sample injector coupled to a Dionex P580 pump. A Phenomenex column (150×4.60 mm, Synergi 4μ hydro-RP 80 Å), kept at a temperature of 25° C. was used for analytical purposes. The HPLC unit was controlled using Chromeleon software. Linear gradient elution using H$_2$O/MeCN systems (containing 0.1% CF$_3$COOH) at flow rates of 1 mL/min was performed. Purity was assessed by integration of chromatograms (λ=254 nm).

ErbB Inhibitors

AG1478 was obtained from Tocris Biosciences. Trastuzumab was obtained from Genentech. Cetuximab was obtained from Imclone. Erlotinib was obtained from Genentech. Gefitinib was obtained from Astra Zeneca. Lapatanib was obtained from Glaxo SmithKline.

Preparation of Seliciclib

Roscovitine was prepared in accordance with the method disclosed in EP0874847B (CNRS). Seliciclib was obtained from Cyclacel (Dundee, UK). (3R)-3-{9-isopropyl-6-[(pyridin-3-ylmethyl)-amino]-9H-purin-2-ylamino}-2-methyl-pentan-2-ol [1], (3S)-3-{9-isopropyl-6-[(pyridin-3-ylmethyl)-amino]-9H-purin-2-ylamino}-2-methyl-pentan-2-ol [2] and (2R3S)-3-{9-isopropyl-6-[(pyridin-3-ylmethyl)-amino]-9H-purin-2-ylamino}-pentan-2-ol [3], and other compounds of formula (I) were prepared in accordance with the methods disclosed in WO2004/016612 (Cyclacel Ltd).

Preparation of (2R,3S-3-(6-((4,6-dimethylpyridin-3-ylmethylamino)-9-isopropyl-9H-purin-2-ylamino)pentan-2-ol [4]

(2R, 3S)-3-Amino-pentan-2-ol was prepared by one or other of two routes differing in the protecting group used for the amine. Further details of compounds of formula (I) may be found in co-pending PCT application <Attorney's reference P29055WO>, claiming priority from GB0706632.7 and U.S. 60/921,897.

Route 1 Employed Trityl as the Protecting Group (S)-2-(Tritylamino)butan-1-ol

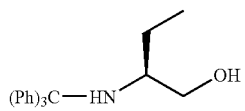

To a stirred solution of (S)-(+)-2-aminobutan-1-ol (10 g, 112.18 mmol) in dichloromethane (DCM, 250 ml) under an argon atmosphere at room temperature, was added diisopropylethylamine (DIEA, 19.4 ml, 112.18 mmol) followed by trityl chloride (31.2 g, 112.18 mmol). The reaction mixture was stirred at this temperature for 48 h, when TLC (hexane:ether:MeOH; 55:40:5) indicated that the reaction had gone to completion. The solvent was evaporated in vacuo and the residue taken up in ethyl acetate. The organic solution was washed with water (2×), dried over sodium sulphate. The solvent was removed to afford (S)-2-(trityl-amino)-butan-1-ol as a light yellow oil;

Yield: 33 g (89%). $^1$H NMR (CDCl$_3$, 250 MHz): δ 0.72 (3 H, t, J=7.5 Hz, —NHCH(CH$_2$CH$_3$)CH$_2$OH), 1.15-1.10 (m, 2 H,—NHCH(CH$_2$CH$_3$)CH$_2$OH), 2.05 (1 H, s, br, NH), 2.24 (1 H, s, br, OH), 2.62-2.54 (m, 1 H, —NHCH(CH$_2$CH$_3$)CH$_2$OH), 3.17-3.08 (1 H m, —NHCH(CH$_2$CH$_3$)CHHOH), 3.35-3.29 (1 H, m, NHCH(CH$_2$CH$_3$)CHHOH), 7.37-7.2 (12 H, m, ArH), 7.65-7.58 (3 H, m, ArH); δ$_C$ (250 MHz, CDCl$_3$) 146.86 (C), 129.43 (6×CH), 127.90 (6×CH), 126.48 (3×CH), 71.27 (C), 62.72 (CH$_2$), 48.91 (CH), 24.55 (CH$_2$), 10.47 (CH$_3$)

(S)-2-(Tritylamino)butyraldehyde

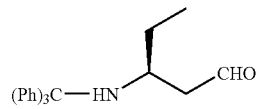

To a stirred solution of dry dimethylsulfoxide (2.4 ml, 2.8 eq, 33.82 mmol) in dry dichloromethane (30 ml) under an argon atmosphere at −78° C., was added oxalyl chloride (2M solution in DCM, 8.45 ml, 1.40 eq, 16.9 mmol), dropwise. The reaction mixture was stirred at −78° C. for 1 h, after which time a solution of (S)-2-(trityl-amino)-butan-1-ol (4 g, 1 eq, 12.07 mmol) in DCM (30 ml) was added dropwise with stirring. The reaction mixture was stirred at this temperature for 2 h after which was added a solution of triethylamine (TEA, 8.4 ml, 5 eq, 60.27 mmol) in DCM (30 ml), and the solution allowed to warm to room temperature over 1 h. The reaction mixture was diluted with more DCM (100 ml) and washed with water (250 ml). The aqueous phase was extracted with DCM (3×50 ml), and the combined organic phase washed with brine (50 ml), dried (Na$_2$SO$_4$) and evaporated in vacuo. The residue was purified by flash silica chromatography (ethyl acetate:Hexane 1:4) to afford (S)-2-(trityl-amino)-butyraldehyde as a light yellow oil; Yield: 3.64 g (91%). $^1$H-NMR (CDCl$_3$, 250 MHz): δ 0.95 (3 H, t, J=7.5 Hz, —NHCH(CH$_2$CH$_3$)CHO), 1.72-1.52 [2 H, m, NHCH(CH$_2$CH$_3$)CHO], 2.76 (1 H, s, br, —NH), 3.41-3.36 [1 H, m, NHCH(CH$_2$CH$_3$)CHO], 7.35-7.17 (12 H, m, ArH), 7.67-7.51 (3 H, m, ArH), 9.05 (1 H, s, NHCH(CH$_2$CH$_3$)CHO). δ$_C$ (250 MHz, CDCl$_3$) 202.95 (CO), 146.23 (C), 129.23 (6×CH), 127.96 (6×CH), 126.85 (3×CH), 71.13 (C), 62.62 (CH), 24.78 (CH$_2$), 10.48 (CH$_3$)

(2R, 3S)-3-(Tritylamino)pentan-2-ol

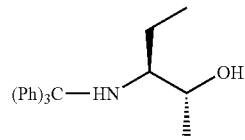

To a stirred suspension of CuBr.SMe$_2$ (3 g, 14.6 mmol) in anhydrous ether (100 ml) under an argon atmosphere at −78° C., was added methyl lithium (1.6M in ether, 16.5 ml, 4.0 eq, 26.5 mmol) dropwise and the solution allowed to warm to room temperature over 1 h. The mixture was recooled to −78° C., and a solution of (S)-2-(trityl-amino)-butyraldehyde (2.2 g, 6.62 mmol) in ether (25 ml) was added dropwise with stirring. The reaction mixture was stirred at this temperature for 2 h then allowed to warm to room temperature over 1 h. A saturated aqueous solution of NH$_4$Cl (50 ml) was added and the two layers separated. The organic phase was washed with brine (50 ml), dried (MgSO$_4$) and evaporated in vacuo. The residue was purified by flash silica gel column chromatography, eluted with hexane:ethyl acetate (80:20) to afford (2R, 3S)-3-(trityl-amino)-pentan-2-ol as a light yellow oil; Yield: 1.5 g (66%). (75% de 2R, 3S: 25% de 2S, 3S). $^1$H-NMR (d<sub>6</sub>-DMSO, 250 MHz): δ 0.0.47+0.55 (2×t, J=7.50+7.26 Hz —NHCH(CH<sub>2</sub>CH<sub>3</sub>)CH(CH<sub>3</sub>)OH), 0.99-1.12 (m, 5 H, —NHCH(CH<sub>2</sub>CH<sub>3</sub>)CH(CH<sub>3</sub>)OH), 2.01 (1 H, m, —NH CH(CH<sub>2</sub>CH<sub>3</sub>)CH(CH<sub>3</sub>)OH), 3.22-3.43 (m, 1H, —NHCH (CH<sub>2</sub>CH<sub>3</sub>)CH(CH<sub>3</sub>)OH), 4.41 [1 H, d, J=3.3, NHCH(CH<sub>2</sub>CH<sub>3</sub>)CH(CH<sub>3</sub>)OH], 7.14-7.56 (15 H, m, ArH). δ<sub>C</sub> (250 MHz, CDCl<sub>3</sub>) 146.88 (C), 128.97 (6×CH), 127.83 (6×CH), 126.43 (3×CH), 71.03 (C), 68.13 (CH), 58.77 (CH), 23.09 (CH<sub>2</sub>), 17.88 (CH<sub>3</sub>), 10.47 (CH<sub>3</sub>)

(2R, 3S)-3-Amino-pentan-2-ol

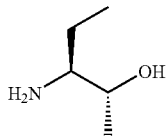

To a stirred solution of (2R,3S)-3-(trityl-amino)-pentan-2-ol (1.64 g, 4.75 mmol) in dichloromethane (20 ml) under an argon atmosphere at room temperature, was added trifluoroacetic acid (10 ml) dropwise, and the solution was stirred at this temperature for 1 h. The solvent was evaporated in vacuo and the residue was precipitated from ether (15 ml) with hexane (150 ml) with stiffing to give a yellow oil. The solvent was decanted from the oil, and the oil was washed with hexane (30 ml) and dried in vacuo to afford (2R, 3S)-3-amino-pentan-2-ol as a light yellow oil; Yield: 0.30 g (98%). (75% de 2R, 3S: 25% de 2S, 3S). <sup>1</sup>H-NMR (d<sub>6</sub>-DMSO, 250 MHz): δ 0.913+0.923 (2×t, 3 H, J=7.50+7.50 Hz, NH<sub>2</sub>CH (CH<sub>2</sub>CH<sub>3</sub>)CH(CH<sub>3</sub>)OH), 1.11+1.18 (3 H, 2×d, J=6.48+6.48 Hz, NH<sub>2</sub>CH(CH<sub>2</sub>CH<sub>3</sub>)CH(CH<sub>3</sub>)OH), 1.41-1.65 (2 H, m, NH<sub>2</sub>CH(CH<sub>2</sub>CH<sub>3</sub>) CH(CH<sub>3</sub>)OH), 2.76+2.93 [2×1 H, m, NH<sub>2</sub> CH(CH<sub>2</sub>CH<sub>3</sub>)CH(CH<sub>3</sub>)OH], 3.61-3.69+3.80-3.90 [2×1 H, m, NH<sub>2</sub>CH(CH<sub>2</sub>CH<sub>3</sub>)CH(CH<sub>3</sub>)OH], 7.73 (2 H, s, br, NH<sub>2</sub>). Route 2 Protected the Amine by Dibenzylation (S)-2-(Dibenzylamino)butan-1-ol

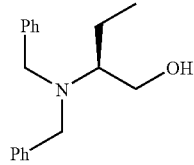 [SMILES: CC[C@@H](CO)N(Cc1ccccc1)Cc1ccccc1]

To a stirred solution of (S)-(+)-2-aminobutan-1-ol (5 g, 56.18 mmol) in dry acetonitrile (100 ml) was added dry powdered potassium carbonate (31 g, 224.72 mmol) followed by benzyl bromide (19 g, 111.11 mmol). The reaction was stirred at room temperature for 24 h. The solvent was removed under vacuo and the residue was taken up in ethyl acetate (100 ml) and water (100 ml). The organic phase was washed again with water, dried (Na<sub>2</sub>SO<sub>4</sub>) and concentrated to provide the pure product as slightly yellow oil (14.5 g, 97.3%). δ<sub>H</sub> (250 MHz, CDCl<sub>3</sub>) 0.98 (3 H, t, J 7.5, CHCH<sub>2</sub>CH<sub>3</sub>), 1.38-1.2 (1 H, m, CHCHHCH<sub>3</sub>), 1.94-1.78 (1 H, m, CHHCH<sub>3</sub>), 2.83-2.71 (1 H, m, CHCHHCH<sub>3</sub>), 3.22 (1 H, s, b, OH), 3.65-3.4 (2 H, m, C H<sub>2</sub>OH), 3.47 (2 H, d, J 17.5, 2×CHHPh), 3.94 (2 H, d, J 17.5, 2×CHHPh), 7.46-7.26 (10 H, m, 2×C<sub>6</sub>H<sub>5</sub>); δ<sub>C</sub> (250 MHz, CDCl<sub>3</sub>) 139.42 (2×C), 129.1 (2×CH), 128.52 (2×CH), 127.25 (2×CH), 61.97 (CH), 60.67 (CH<sub>2</sub>), 53.23 (CH<sub>2</sub>), 17.92 (CH<sub>2</sub>), 11.83 (CH<sub>3</sub>); m/z 270.2 (M+H)

(S)-2-(Dibenzylamino)butanal

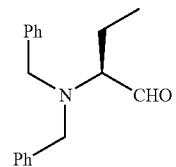

A 2M solution of oxalyl chloride in dichloromethane (3.18 ml, 6.36 mmol) was cooled to −78 0° C. and diluted with dry dichloromethane (20 ml) under dry nitrogen. A solution of dimethylsulfoxide (1 g, 12.72 mmol) in anhydrous dichloromethane was added dropwise to the cooled stirred solution. The reaction was stirred for a further 1 h after completion of addition. A solution of (S)-2-(dibenzylamino) butan-1-ol (1.43 g, 5.3 mmol) in dichloromethane was added over 5 minutes. After 10 minutes, diisopropylethylamine (2.73 g, 21.2 mmol) was added. The reaction was allowed to warm to room temperature and left stiffing for 1 h. It was cooled to 0° C. and ethyl acetate/water (50 ml: 50 ml) was added. The organic layer was washed with water (50 ml), brine (50 ml) dried (MgSO<sub>4</sub>) and concentrated. The product was purified by flash silica column chromatography (ethyl acetate:Hexane 1: 4) to provide the pure product (1.28 g, 90.5%). δ<sub>H</sub> (250 MHz, CDCl<sub>3</sub>) 0.88 (3 H, t, J 7.5, CHCH<sub>2</sub>CH<sub>3</sub>), 1.77-1.54 (2 H, m, CH<sub>2</sub>CH<sub>3</sub>), 2.99 (1 H, t,J 7.5, CHCH<sub>2</sub>CH<sub>3</sub>), 3.74-3.57 (4 H, m, 2×CH<sub>2</sub>Ph), 7.31-7.11 (10 H, m, 2×C<sub>6</sub>H<sub>5</sub>) 9.64 (1 H, s, CHO); δ<sub>C</sub> (250 MHz, CDCl<sub>3</sub>) 203.9 (CO), 139.33 (2×C), 128.99 (4×CH), 128.45 (4×CH), 127.3 (2×CH), 68.46 (CH), 54.85 (CH<sub>2</sub>), 17.44 (CH<sub>2</sub>), 11.83 (CH<sub>3</sub>); m/z 268.2 (M+H)

(2R,3S)-3-(Dibenzylamino)pentan-2-ol

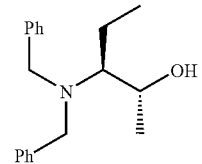 [SMILES: CC[C@@H]([C@@H](C)O)N(Cc1ccccc1)Cc1ccccc1]

To a stirred suspension of CuBr.SMe<sub>2</sub> (1.54 g, 7.5 mmol) in anhydrous ether under an argon atmosphere at −78° C., was added methyllithium (1.6M in ether, 9.4 ml, 15 mmol) dropwise. After the addition was complete, the reaction was allowed to warm to room temperature. The reaction was recooled to −78° C. and a solution of (S)-2-(dibenzylamino) butanal (1 g, 3.75 mmol) in ether (20 ml) was added dropwise. After the addition, continued stirring for 2 h The reaction was then quenched with a saturated aqueous solution of NH<sub>4</sub>Cl (10 ml). The reaction mixture was extracted with ether (2×30 ml) and the combined organic phase washed with brine (20 ml), dried (MgSO<sub>4</sub>) and evaporated in vacuo. The residue was purified by flash silica gel gradient column chromatography, eluted with hexane:ethyl acetate (100:0→80:20) to afford the product as a light yellow oil (0.95 g, 89%) as the only isomer. δ<sub>H</sub> (250 MHz, CDCl<sub>3</sub>) 1.05 (3 H, t, J 7.5, CHCH<sub>2</sub>CH<sub>3</sub>), 1.25 [3 H, d, J 7.5, CH(CH<sub>3</sub>)OH], 1.6-1.49 (1 H, m, CHHCH<sub>3</sub>), 1.88-1.73 (1 H, m, CHHCH<sub>3</sub>), 2.41 (1 H, s, br, OH), 2.66-2.59

(1 H, m, C<u>H</u>CH₂CH₃), 3.85-3.65 (4 H, m, 2×C<u>H</u>₂Ph), 4.05-3.9 (1 H, m, C<u>H</u>OH), 7.41-7.25 (10 H, m, ArH) δ$_C$ (250 MHz, CDCl₃) 140.05 (2×C), 128.98 (4×CH), 128.37 (4×CH), 127.3 (2×CH), 66.81 (CH), 63.65 (CH), 55.41 (CH₂), 20.63 (CH₃) 18.44 (CH₂), 12.5 (CH₃)

Example 1

2-Chloro-4,6-dimethylnicotinonitrile

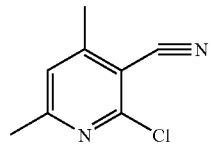

4,6-Dimethyl-2-oxo-1,2-dihydropyridine-3-carbonitrile (5 g, 34 mmol) was added to phosphorus oxychloride (20 ml). The reaction was stirred at reflux for 2 h, after which it was seen complete. Volatiles were removed and the residue triturated with petrol. The resultant solid was filtered off and washed with hexane, and dried to give a pure white solid (5.1 g, 90%). δ$_H$ (250 MHz, CDCl₃) 2.55 (3 H, s, CH₃), 2.57 (3 H, s, CH₃), 7.09 (1 H, s, ArH); δ$_C$ (250 MHz, CDCl₃) 162.64 (C), 154.39 (C), 152.26 (C), 123.22 (CH), 114.28 (C), 108.31 (C), 24.5 (CH₃), 20.54 (CH₃); m/z 189 (M+Na)

4,6-Dimethylpyridin-3-ylmethyl Carbamic Acid t-butyl Ester

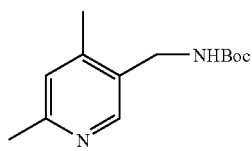 [SMILES: Cc1cc(C)c(CNC(=O)OC(C)(C)C)cn1]

2-Chloro-4,6-dimethyl-nicotinonitrile (5 g, 30.1 mmol) was dissolved in 10% acetic acid/ethanol (30 ml). 10% palladium over charcoal catalyst (0.5 g) was added and the reaction stirred under an atmosphere of hydrogen for 24 h. at 60° C. The mixture was filtered through a pad of celite. Volatiles were removed and the crude residue dissolved in dichloromethane (30 ml). To the stirred solution was then added triethylamine (5 ml) followed by di-tert-butyldicarbonate (6.5 g, 30 mmol). After 3 h, the solvent was removed and the residue dissolved in ethyl acetate. It was washed with water (50 ml), saturated bicarbonate (50 ml), dried and evaporated. The crude product was purified by silica gel flash column chromatography (ethyl acetate:hexane 1:2) to provide 1.4 g of pure title compound (20% yield). δ$_H$ (250 MHz, CDCl₃) 1.43 (9 H, s, 3×CH₃) 2.19 (3 H, s, CH₃), 2.38 (3 H, s, CH₃), 4.19 (2 H, s, br, ArC<u>H</u>₂NH), 6.84 (1 H, s, ArH), 8.15 (1 H, s, ArH); δ$_C$ (250 MHz, CDCl₃) 157.41 (CO), 155.63 (C), 148.93 (CH), 145.91 (C), 129.51 (C), 124.76 (CH), 79.44 (C), 46.12 (CH₂), 28.32 (3×CH₃), 23.74 (CH₃), 18.97 (CH₃); m/z 237.2 (M+H)

(4,6-Dimethylpyridin-3-ylmethyl)-(2-fluoro-9H-purin-6-yl)-amine

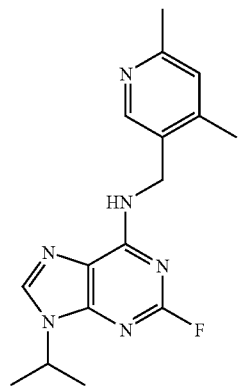 [SMILES: Cc1cc(C)c(CNc2nc(F)nc3c2ncn3C(C)C)cn1]

To a stirred solution of 6-chloro-2-fluoropurine (0.83 g, 4.9 mmol) in n-BuOH (50 ml) under an argon atmosphere at 0° C., was added DIEA (2.5 ml, 14.7 mmol) followed by (4,6-dimethylpyridine-3-yl)methanamine (1 g, 7.35 mmol). The reaction mixture was stirred at this temperature for 1 h and then allowed to return to room temperature and stirred for 4 h, it was still seen incomplete, hence heated the reaction to 100° C. and left at that temperature for 2 h. The solvent was evaporated in vacuo and the residue was purified by gradient flash column chromatography on silica gel, eluted with CHCl₃:MeOH (100:0→90:10), to afford the product as a white solid; Yield: 0.86 g (65%); δ$_H$ (250 MHz, CDCl₃) 2.35 (3 H, s, CH₃), 2.39 (3 H, s, CH₃), 4.61 (2 H, s, br, NHC<u>H</u>₂), 7.07 (1 H, s, ArH), 8.13 (1 H, s, ArH), 8.33 (1 H, s, ArH), 8.69 (1 H, s, br, NH); δ$_C$ (250 MHz, CDCl₃) 161.2 (C), 158.57 (C), 156.08 (C), 150 (C), 148.08 (CH), 148.14 (CH), 147.9 (CH), 145.93 (C), 129.92 (C), 129.76 (C), 124.37 (CH), 41.7 (CH₂), 23.17 (CH₃), 18.14 (CH₃); m/z 273.2 (M+H)

(4,6-Dimethylpyridin-3-ylmethyl)-(2-fluoro-9-isopropyl 9H-purin-6-yl)-amine

To a stirred solution of (4, 6-dimethyl-pyridin-3-ylmethyl)-(2-fluoro-9H-purin-6-yl)-amine (0.6 g, 1.9 mmol) in DMF (10 ml) under an argon atmosphere, at RT, was added K₂CO₃ (powdered, anhydrous, 1.77 g, 5 eq, 13 mmol) followed by 2-bromopropane (1.8 ml, 10 eq, 19 mmol). The reaction mixture was stirred at RT for 24 h, when TLC (CHCl₃: MeOH; 90:10) indicated that the reaction had gone to completion. The solvent was evaporated in vacuo and the residue partitioned between water (50 ml) and ethyl acetate (50 ml), the aqueous phase was separated and extracted with more EtOAc (2×50 ml). The bulked organic phase was washed with brine (50 ml), dried (MgSO₄) and evaporated in vacuo, and the residue was purified by gradient column chromatography on silica gel, eluted with CHCl₃:MeOH (100:0→95:5), to provide the product as a yellow film (0.4 g, 59%). $\delta_H$ (250 MHz, CDCl₃) 1.52 [6 H, d, J 7.5 CH(C$\underline{H}_3$)₂] 2.27 (3 H, s, CH₃), 2.45 (3 H, s, CH₃), 4.73-4.62 (3 H, m, NHC$\underline{H}_2$ and C$\underline{H}$[CH₃]₂), 6.91 (1 H, s, ArH), 7.12 (1 H, NH), 7.47 (1 H, s, ArH), 8.32 (1 H, s, ArH); $\delta_C$ (250 MHz, CDCl₃) 160.77 (C), 157.89 (C), 157.43 (C), 156.12 (C), 155.79 (C), 149.14 (CH), 137.7 (CH), 128.7 (C), 129.76 (C), 124.83 (CH), 47.2 (CH), 40.14 (CH₂), 23.9 (CH₃), 22.47 (2×CH₃), 18.54 (CH₃); m/z 315.3 (M+H)

(2R,3S-3-(6-((4,6-Dimethylpyridin-3-ylmethylamino)-9-isopropyl-9H-purin-2-ylamino)pentan-2-ol

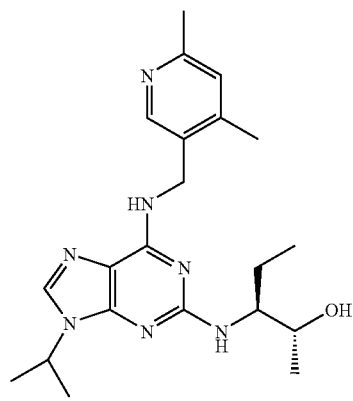 [SMILES: CC[C@H](Nc1nc(NCc2cnc(C)cc2C)c2ncn(C(C)C)c2n1)[C@@H](C)O]

To a stirred solution of (4,6-dimethyl-pyridin-3-ylmethyl)-(2-fluoro-9-isopropyl-9H-purin-6-yl)-amine (300 mg, 0.84 mmol) in n-BuOH/DMSO (5 ml, 4:1) at room temperature under an argon atmosphere was added DIEA (1.7 ml, 10 eq, 8.4 mmol) followed by (2R,3S)-3-amino-pentan-2-ol (0.5 g, 4.8 mmol) The flask was fitted with a condenser and the reaction mixture was placed in a preheated oil bath at 140° C. and stirred at this temperature for 72 h. The reaction mixture was allowed to cool to room temperature and the solvent was evaporated in vacuo. The residue was partitioned between ethyl acetate (50 ml) and water (50 ml), the aqueous phase was extracted with more EtOAc (2×25 ml), and the combined organic phase was washed with brine (50 ml), dried (MgSO₄) and evaporated in vacuo. The residue was purified by flash gradient column chromatography on silica gel eluted with CHCl₃: MeOH (100:0→95:5), to afford 55 mg of pure title compound (12%). $\delta_H$ (250 MHz, CDCl₃) 0.95 (3 H, t, J 7.5, CHCH₂C$\underline{H}_3$), 1.06 (3 H, d, J 7.5, CHC$\underline{H}_3$OH) 1.48 [6 H, d, J 7.5 CH(C$\underline{H}_3$)₂], 2.24 (3 H, s, CH₃), 2.4 (3 H, s, CH₃), 3.92-3.82 (2 H, m, NHCH₂), 4.67-4.45 (3 H, m, C$\underline{H}$EtC$\underline{H}$MeO$\underline{H}$), 6.15 (1 H, s, br, NH), 6.87 (1 H, s, ArH), 7.37 (1 H, ArH), 8.31 (1 H, s, ArH); $\delta_C$ (250 MHz, CDCl₃) 160.11 (C), 157.68 (C), 154.57 (C), 149.42(CH), 146.38 (C), 134.54 (CH), 129.24 (C), 124.84 (CH), 71.52 (CH), 59.65(CH), 46.47 (CH), 40.33 (CH₂), 24.94 (CH₂), 23.89 (CH₃), 23.52 (2×CH₃), 17.37 (CH₃), 12.57 (CH₃); m/z 398.3 (M+H)

Abbreviations

The abbreviations used are: CTD, Carboxyl terminal domain; DMEM, Dulbecco's modified Eagle's medium; DMSO, Dimethylsulphoxide; EGF, Epidermal Growth Factor; EGFR, Epidermal Growth Factor Receptor; ERK, extracellular signal regulated kinase; FCS, Foetal calf serum; NSCLC, Non-small cell lung cancer; PARP, poly-ADP ribose polymerase; PBS, Phosphate-buffered Saline; PKB, protein kinase B; SDS-PAGE, sodium dodecyl sulphate-polyacrylamide gel electrophoresis Cell Lines, Cell Culture and Reagents MCF7, A549, H460, SkBr3, H1650 and H358 cells were purchased from the ATCC (Mannassas, USA). Cell cultures were maintained in DMEM, except for H1650 and H358 cells, which were grown in RPMI medium. Cells were cultured at 37° C. in a humidified atmosphere of 5% CO₂ in media containing 10% (v/v) foetal calf serum (FCS), 100 Units/ml penicillin and 100 µg/ml streptomycin. All reagents were purchased from Sigma (Poole, UK) unless stated otherwise.

Drug Combination Analysis

Experiments were performed in 96-well plates. SkBr3 and MCF7 cells were seeded at a density of 5,000 cells/well, in media containing 1% (v/v) FCS. H358, H1650 and H460 cells were seeded at 3,000 cells/well, and A549 cells at 2,000 cells/well, in media containing 10% (v/v) FCS. Stock solutions of seliciclib (Cyclacel Ltd., Dundee, UK) and AG1478 (Tocris Bioscience, Bristol, UK) were prepared in dimethyl sulphoxide (DMSO), while trastuzumab (Genentech Inc, South San Francisco, USA) was dissolved in 0.9% (w/v) sterile saline solution. Serial dilutions (1.5-fold) for each compound were prepared, with the concentration range spanning the $IC_{50}$ value of each drug.

For experimental assessment of potential synergistic interactions, the concomitant treatment regime involved simultaneous treatment of cells with seliciclib and either trastuzumab or AG1478 for 72 h, alongside suitable controls of cells treated with the individual compounds alone for 72 h. In the sequential treatment regimes, one drug was added to the cells 2 h after plating, and left for 24 h. Media was then aspirated, replaced with fresh media containing the second drug and incubated for a further 72 h. The two individual treatment controls for the sequential treatment regime involved substituting one of the drug treatments with drug-free media. All treatments were performed in triplicate wells.

After drug treatment, the number of viable cells in each well was estimated by incubating for 1 h in media containing 10% alamar blue (Roche, Lewes, East Sussex, U.K.) and measuring the absorbance at 488-595 nm. Drug interactions were analysed using the Calcusyn software package (BioSoft, Cambridge, U.K.), which is based on the median effect model of Chou and Talalay [19]. A Combination Index (C.I.) of 1 indicated an additive drug interaction, whereas a C.I. greater than 1 was antagonistic and a score lower than 1 was synergistic.

Western Blot Analysis

Cells were seeded at approximately 8×10⁵ cells/plate on 10 cm plates and left to settle overnight. Compounds were added to the plates and cells were incubated for the indicated times. Media was removed from each of the wells and centrifuged at 1,000×g for 5 min to pellet any cells that had become detached from the plate surface. Cells that remained attached to the plate were washed once with ice-cold buffer A (50 mM HEPES, pH 7.0, containing 20 mM NaCl, 1 mM DTT, and protease inhibitor cocktail (Merck, Nottingham, U.K.)), then scraped into 0.350 ml buffer B (buffer A containing 10 mM sodium pyrophosphate, 10 mM sodium fluoride and 1 mM sodium orthovanadate). The resuspended cells were then pooled with the appropriate media cell pellet and lysed by sonication (2×3s bursts using Sanyo soniprep 150 at 5 amp). The protein concentration of each lysate was determined using the BCA assay (Perbio Science, Northumberland, U.K.). Lysates (20-30 µg protein/well) were resolved on 3-8% acrylamide Tris-acetate gels or 10% acrylamide Bis-Tris gels (Invitrogen, Glasgow, U.K.) and the proteins transferred to nitrocellulose membranes (Schleicher & Schuell, London, U.K.) using the Invitrogen wet transfer system. Membranes were blocked for 1 h at room temperature in PBS containing 0.02% (v/v) Tween 20 (PBST) and 5% (w/v) fat-free dried milk. Primary antibody incubations were carried out overnight at 2-8° C. in PBST containing 3% (w/v) dried milk, using the following primary antibodies: ErbB2 (Calbiochem, Nottingham, U.K.), EGFR (Calbiochem), phospho-Tyr1068 EGFR (New England Biolabs, Hertfordshire, U.K.), cyclin D1 (Lab Vision, Suffolk, U.K.), phospho-Thr185 ERK1 and phospho-Thr202 ERK2 (Abcam, Cambridge, U.K.), ERK2 (Abcam), Asp-214 cleaved PARP (BD Pharmingen, Oxford, UK.) and β-Actin. Membranes were washed three times in PBST, and then incubated for 1 h with the appropriate horseradish peroxidase-conjugated secondary antibody (Perbio) at 1:5000 dilution in PBST containing 3% (w/v) milk. Membranes were washed three times in PBST prior to development using an enhanced chemiluminescence kit (Amersham Corporation, Buckinghamshire, U.K.).

Flow Cytometry

H358 or H1650 cells were seeded in 10 cm plates at approximately $5\times10^5$ cells/plate and left to settle overnight. Cells were treated with $1\times IC_{50}$ seliciclib, AG1478 or both drugs together. After 72 h treatment, cells were harvested by trypsinisation, washed twice in PBS and then fixed overnight in 70% (v/v) ethanol at −20° C. Cells were washed twice in PBS containing 1% (w/v) BSA, then incubated with 50 µg/ml propidium iodide and 50 µg/ml ribonuclease A for 20 min at room temperature. Cells were analysed for DNA content by flow cytometry using the CellQuest programme on a Becton Dickinson LSR flow cytometer.

In vivo Studies

Female (nu/nu) mice were injected subcutaneously with ~$1\times10^7$ H358 cells/mouse at a single site on their flanks. Tumours were allowed to grow to ~110 mm³ before being pair-matched by tumour size into treatment groups (9 mice/group). One group was treated with seliciclib (50 mg/kg) as a twice daily intraperitoneal injection for five consecutive days followed by a two day break; the treatment was then repeated for a total of four cycles. Erlotinib (100 mg/kg) was given daily by oral gavage for 28 consecutive days. The group treated with the combination were dosed in the same manner as both single agent groups. Mice were weighed at least twice a week to assess toxicity of the treatments and the tumours were measured with calipers at least twice a week to determine tumour growth. During the first week of treatment there was some weight loss in the animals. However, this appeared to be associated with the initial vehicle used for seliciclib (50 mM HCl) as the weight loss also occurred in the vehicle control group (max weight loss 11% between days 8-11). On Day 10 the vehicle was changed to 10% cremophor, 10% ethanol, 80% saline for the control and the two groups receiving seliciclib; all three groups started gaining weight immediately. Tumour measurements were converted into volumes using the formula: tumour volume (mm³)=width² (mm)× length (mm)×0.52. The percent tumour growth inhibition was determined with the formula: 1−(change in treated tumour volume/change in control tumour volume)×100. For each group statistical significance was determined by comparing to the control group using a one-way ANOVA followed by a Dunnett's test. Significance between different treatment groups was determined using a two sided unpaired Student's T-test.

Results and Discussion

Compounds that target CDKs or members of the ErbB family have attracted significant interest as cancer therapeutics. Inhibitors of either of these kinase families have shown some clinical activity as single agents, but are ultimately more likely to be used in combination with other drugs [20]. The aim of this series of experiments was to determine whether inhibitors of these two protein kinase families can be combined synergistically.

To evaluate the interaction between seliciclib and trastuzumab, combination experiments were performed in breast cancer cell lines; either SkBr3, which overexpresses HER2, or MCF7, which expresses low levels of HER2 [15]. Incubation with trastuzumab (1-100 nM) reduced proliferation of SkBr3 cells by up to 40%, but had no significant effect on MCF7 cells (data not shown), in agreement with previous data [15]. Seliciclib inhibited the growth of both cell lines with an $IC_{70}$ of 20.4 µM and 15.4 µM in SkBr3 and MCF7 cells respectively. Co-incubation of seliciclib and trastuzumab resulted in a moderately synergistic inhibition of cell growth in the SkBr3 cell line (Table 1) generating a Calcusyn combination index (CI) of 0.73 at $ED_{50}$ (the point at which the combination inhibits cell growth by 50%). Mitogenic stimuli transduced by the HER2 signalling pathway result in the expression of cyclin D1 and the consequent activation of CDKs leading to cellular proliferation [3]. Thus overexpression or constitutive activation of these receptors results in oncogenic transformation. Indeed it has been shown that cyclin D is required for transformation by the HER2 receptor [21], and cyclin D1-deficient mice are resistant to HER2-mediated tumorigenesis [22, 23]. To evaluate the mechanism behind the synergistic seliciclib/trastuzumab combination, analysis of the effects on the HER2 signalling pathway was performed. SkBr3 cells were incubated with seliciclib, trastuzumab or the combination of both agents for 24 h, cell lysates were prepared and the levels of HER2 and cyclin D1 proteins examined by western blot. Trastuzumab treatment had a modest effect on HER2 levels, at concentrations up to 28 nM (FIG. 1A), which is consistent with previous findings that demonstrated that this drug does not dramatically downregulate HER2 levels in SkBr3 cells [24]. On the other hand, treatment with seliciclib alone decreased HER2 levels in a dose-dependent manner (FIG. 1B). The downregulation of HER2 receptor levels by seliciclib was most likely due to its inhibitory effects on CDKs 7 and 9 [25, 26] resulting in decreased transcription of the receptor and loss of the HER2 protein as it is naturally turned over within the cell [27]. Trastuzumab and seliciclib when administered together produced greater downregulation of the HER2 receptor than either single agent treatment alone, suggesting that the drugs synergistically downregulate the levels of this receptor (FIG. 1C).

As one of the final downstream components of the HER2 signalling pathway, it was of interest to examine the effect of the combination on cyclin D1 protein levels. At the concentrations tested in these experiments, trastuzumab treatment alone had no apparent effect on cyclin D1 levels (FIG. 1A), while seliciclib significantly decreased cyclin D1 levels in a dose-dependent manner (FIG. 1B). This loss of cyclin D1 was slightly enhanced by combining seliciclib with trastuzumab (FIG. 1C). Cyclin D1 levels would most likely have been downregulated as a consequence of decreased HER2 signalling and also by seliciclib-mediated inhibition of cyclin D1 transcription [12]. These data indicate that in SkBr3 cells, seliciclib enhanced the efficacy of trastuzumab against the HER2 signalling pathway by promoting the downregulation of the HER2 receptor and loss of the cell cycle regulator cyclin D1, which has been shown to be critical for propagating the HER2 mitogenic signal [21-23].

To extend the analysis of the synergistic interactions between seliciclib and inhibitors of ErbB family members, seliciclib was tested in combination with the EGFR tyrosine kinase inhibitor AG1478 [18, 28], an analogue of erlotinib. Erlotinib has been approved for the treatment of advanced NSCLC having shown survival benefit in the treatment of lung cancer in clinical trials [29]. The combination between seliciclib and AG1478 was evaluated initially in three NSCLC cell lines: NCI-H358, A549 and NCI-H460. These cell lines express different levels of wild type EGFR with A549 cells expressing the highest levels of this receptor and H358 cells the least (FIG. 2). The $IC_{50}$ values for AG1478 were 4 µM, 6.6 µM, and 10.4 µM in H358, A549 and H460 cells respectively, demonstrating that there was no direct correlation between EGFR protein levels and sensitivity to AG1478. An equivalent pattern of sensitivity has been reported for erlotinib, leading to the description of these three cell lines as sensitive, intermediate and resistant respectively [30]. Combination analysis was performed evaluating concomitant incubations and sequential additions (both orientations). In H358 cells, concomitant drug treatment and pre-treatment with AG1478 followed by seliciclib caused synergistic inhibition of cell growth ($ED_{50}$ CI values of 0.74 and 0.81 respectively (Table 2).

To elucidate the molecular mechanism involved in the synergistic effects of seliciclib and AG1478, H358 cells were treated with either agent alone or in combination at concentrations equivalent to those used for the cytotoxicity analysis; cell lysates were prepared and proteins analysed by western blotting (FIG. 3). Initially the effects of the compounds on the levels of the EGFR and its phosphorylation status were studied. Treatment with either AG1478 or seliciclib decreased the level of the EGFR in a dose-dependent manner. When AG1478 and seliciclib were applied together, the EGFR protein levels were decreased more effectively than with either of the two individual drug treatments, suggesting that the drugs were promoting synergistic downregulation of the receptor (FIG. 3). Moreover, AG1478 treatment resulted in a dose-dependent decrease in EGFR phosphorylation, while seliciclib treatment had a limited effect. The reduction in the levels of EGFR phosphorylation was enhanced by the concomitant treatment, suggesting that the compounds were synergistically downregulating the quantity and activation status of the EGFR.

To further explore the effects of the combination of seliciclib and AG1478 on the EGFR signalling pathway, two downstream components of the pathway were analysed; the phosphorylation status of ERK, and cyclin D1 protein levels. Seliciclib alone had no significant effect on ERK phosphorylation at the concentrations tested. AG1478, on the other hand, stimulated ERK phosphorylation at low concentrations, an effect that has also been observed with gefitinib in NSCLC cell lines [31], while having minimal effect at higher concentrations. However, the combination was very effective at reducing ERK phosphorylation, producing a clear decrease in the levels of phospho-ERK, suggesting an inhibition of EGFR signalling. Cyclin D1 lies downstream of the majority of ErbB receptor signalling pathways in its role as one of the key regulators of the cell cycle. Indeed a reduction in cyclin D1 levels has been shown to be essential to obtain a response to EGFR inhibitors both in vitro and in patients [32, 33]. Seliciclib concentrations at or above cellular $IC_{50}$ values produced a modest decrease in cyclin D1 levels in H358 cells, while at the concentrations tested AG1478 had very little effect on the levels of this protein. However, when applied together, the two drugs dramatically reduced cyclin D1 expression in a dose-dependent manner (FIG. 3). Once again seliciclib's contribution to the synergistic interaction was most likely due to the inhibition of CDKs 7 and 9, leading to a reduction in the levels of key components of the EGFR signalling pathway.

Seliciclib treatment is known to cause apoptotic cell death [11, 34], but significant induction of apoptosis is not observed in many cell lines treated with AG1478, erlotinib or trastuzumab [17, 35-37]. Hence a synergistic induction of apoptosis was not anticipated when seliciclib and AG1478 were combined. Using PARP cleavage as a marker of apoptosis, western blot analysis demonstrated that at the AG1478 concentrations tested in H358 cells, there was no increase in PARP cleavage (FIG. 3). In contrast, seliciclib induced a dose-dependent increase in cleaved PARP but this was not enhanced in the presence of AG1478 (FIG. 3). Taken together, these results suggest that in H358 cells, the combination of seliciclib and AG1478 caused a synergistic inhibition of cell growth, primarily through the downregulation of the EGFR signalling pathway, resulting in a cessation of cell proliferation rather than an increased induction of apoptotic cell death.

To explore the induction of apoptosis in more detail these studies were expanded to evaluate the combination in the NCI-H1650 NSCLC cell line. This cell line expresses a mutant EGFR and was reported to be very sensitive to erlotinib, with apoptosis being induced following erlotinib treatment [38]. Calcusyn analysis suggested that the seliciclib/AG1478 combination was slightly more synergistic in the H1650 cell line than in the H358 cells (data not shown). To evaluate the effect of the combination on apoptosis, H1650 and H358 cells were treated with the compounds at their appropriate cytotoxic $IC_{50}$ concentration and the induction of apoptosis determined both by western blot analysis for the level of cleaved PARP and by flow cytometry analysis for the number of cells containing a sub-G1 DNA content. As previously demonstrated, (FIG. 3) at the $IC_{50}$ concentration neither single agent nor the combination had a significant effect on the induction of cleaved PARP in H358 cells (FIG. 4A). The small amount of cleaved PARP in the DMSO control represented the natural apoptotic turnover within this cell line that was not increased by any of the treatments. In contrast, in H1650 cells both seliciclib and AG1478 caused a small increase in the levels of cleaved PARP when compared to the DMSO treated control. Moreover following treatment with the combination the increase in cleaved PARP was greater than either of the single agents alone (FIG. 4A). Flow cytometry analysis of cells from the same experiment showed the characteristic increase in G2/M phase cells following seliciclib treatment for both H358 and H1650 cells (FIG. 4B). In H358 cells none of the treatments led to a significant increase in cells containing a sub-G1 DNA content (apoptotic cells) above the ~10% present in the DMSO treated control cells. In H1650 cells the control cells had a very low number of cells with a sub-G1 content (~2.5%); both single agent treatments led to small increases in the sub-G1 population and the combination led to a greater increase in the apoptotic population (FIG. 4B) in a manner analogous to the cleaved PARP data (FIG. 4A). Equivalent results were obtained in H1650 cells if the treatment concentrations were increased to 1.5 times or 2.25 times the cytotoxic $IC_{50}$ value but importantly in each case a greater percentage of apoptotic cells was detected (data not shown). These data suggest that in cell lines that are susceptible to the induction of apoptosis following AG1478 treatment, the combination with seliciclib will result in greater levels of apoptotic induction.

Finally the combination of seliciclib and erlotinib was evaluated in vivo in an H358 NSCLC xenograft model. Mice bearing H358 tumours of ~110 mm$^3$ were given seliciclib (50 mg/kg) intraperitoneally twice per day for five consecutive days and then after a two day treatment break this schedule was repeated for a total of 28 days. Erlotinib (100 mg/kg) was dosed by oral gavage once per day for 28 consecutive days, while for combination treatment mice received the same schedule as for each single agent. Control mice received seliciclib vehicle on a twice daily schedule. On day 49, three weeks after all treatments had ceased, control mice had tumours with a mean volume of 700 mm$^3$ which represented a >6 fold increase in tumour size (FIG. 5). Mice treated with single agent seliciclib or erlotinib had mean tumour volumes of 717 mm$^3$ and 444 mm$^3$ respectively which indicated that neither agent had significant activity on their own at these doses. The low level of erlotinib activity (44% tumour growth inhibition p>0.05) correlated with the modest activity reported previously for this tumour type [30]. However, by day 49, mice treated with the combination of seliciclib and erlotinib had a mean tumour volume of 153 mm$^3$ which represented 93% tumour growth inhibition. When all the groups were compared to the vehicle control using an ANOVA followed by Dunett's multiple comparison test, the only group that was statistically different was the combination group (p<0.01). If the individual groups were compared against each other using a Student's T test then the combination was also statistically significant from the single agent seliciclib and erlotinib treatments (p<0.002). The optimal T/C ratio (ratio of median treated tumour volume to median control tumour volume expressed as a percentage) was 22% by Day 49. Therefore in this H358 xenograft while neither erlotinib nor seliciclib was particularly efficacious when used as a single agent, the combination of the two compounds led to significant tumour growth delay.

The data presented in this manuscript shows that CDK inhibitors such as seliciclib can interact synergistically with inhibitors of ErbB signalling pathways to prevent cell growth. This data represents the first report of synergy between CDK inhibitors and EGFR inhibitors. Importantly the combination of seliciclib and AG1478 was synergistic in cells that expressed either mutant EGFR or wild type EGFR. Significantly the combination between seliciclib and erlotinib showed dramatic synergy in vivo in a wild type EGFR expressing H358 xenograft model. At the molecular level, synergy appeared primarily to involve augmented downregulation of ErbB receptor levels and inhibition of downstream signalling, resulting in an enhanced loss of Cyclin D1, one of the key downstream components of ErbB signalling pathways. As combination of seliciclib with inhibitors of the ErbB receptor family appeared to act synergistically at a mechanistic level, so the combination of these agents could potentially improve the clinical efficacy of ErbB inhibitors, and also expand the number of tumours sensitive to these agents. These data suggest that these combinations are worthy of further investigation.

Examining the in vitro and in vivo Synergy Between Seliciclib or Second Generation cdk Inhibitors and Other EGFR or Her2 Inhibitors in H292 and SkBr3 Cells H292 cells were treated with various concentrations of (i) seliciclib or the second generation inhibitors [1]-[4], (ii) ErbB inhibitors AG1478 erlotinib, gefitinib or lapatinib, or (iii) combinations thereof, for 72 hours. Cells were incubated with Alamar blue reagent and the absorbance readings were analysed by Calcusyn to obtain 50%, effective dose values. Experiments were repeated at least 3 times in triplicate. The results are shown in Table 3 below.

Experiments were also performed with seliciclib or compound [4] in combination with lapatinib in the Her2 over expressing breast cancer cell line SkBr3 to evaluate the synergistic effect of targeting the Her2 signalling pathway (Table 4).

For all of the second generation compounds, significant synergy was observed at ED50, in line with what was observed with seliciclib.

These promising results were followed up in vivo, using an H292 xenograft model. Tumour cells were injected into nude mice and allowed to grow to approximately 130 mm$^3$. At this time treatment was initiated. Groups of mice were administered vehicle, seliciclib, erlotinib or both compounds for approximately 2 weeks. Mice were monitored for signs of toxicity and the tumours were measured every 2-3 days and plotted in the graph below. Seliciclib or (3R)-3-{9-isopropyl-6-[(pyridin-3-ylmethyl)-amino]-9H-purin-2-ylamino}-2-methyl-pentan-2-ol [1] were administered on days 1-5 and 11-15 at 50 mg and 40 mg bid respectively, and erlotinib was given on days 1-7 and 11-15. Dosing with erlotinib was initiated at 100 mg qd po for the first 7 days but was reduced to 50 mg qd po from day 11.

Seliciclib and (3R)-3-{9-isopropyl-6-[(pyridin-3-ylmethyl)-amino]-9H-purin-2-ylamino}-2-methyl-pentan-2-ol [1] had minimal if any effect on tumour growth as single agents at these doses (FIG. 6). Erlotinib was moderately effective as a single agent at this dose. The combination of erlotinib with seliciclib was slightly better than erlotinib alone, but the most dramatic effect was obtained by combining (3R)-3-{9-isopropyl-6-[(pyridin-3-ylmethyl)-amino]-9H-purin-2-ylamino}-2-methyl-pentan-2-ol [1] and erlotinib. On day 8 both combinations were found to be significantly different from the erlotinib single agent treatment (p~0.02). However, thereafter only the (3R)-3-{9-isopropyl-6-[(pyridin-3-ylmethyl)-amino]-9H-purin-2-ylamino}-2-methyl-pentan-2-ol [1] and erlotinib combination remained statistically significant, reaching p=0.007 on day 15.

Taken together, this data demonstrates that combinations of CDK inhibitors such as seliciclib or second generation inhibitors such as compounds [1]-[4] with EGFR inhibitors are synergistic in vitro and in vivo.

Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

TABLE 1

Seliciclib in combination with trastuzumab in SkBr3 cells.

| Cell line | Schedule | CI at $ED_{50}$ |
|---|---|---|
| SkBr3 | seliciclib + trastuzumab | 0.73 |

Seliciclib and trastuzumab were tested in combination in SkBr3 cells, using the protocol described in Methods and Materials. A concomitant treatment regime was used, and the resulting Combination Index values (CI) shown for $ED_{50}$ (the point on the curve where cellular proliferation is inhibited by 50%). Results are the average of at least three independent experiments. The CI values definitions are: 1.1-0.9 is additive, 0.9-0.85 is slightly synergistic, 0.85-0.7 is moderately synergistic, 0.7-0.3 is synergistic.

TABLE 2

Seliciclib in combination with the EGFR inhibitor AG1478 in NSCLC cell line H358

| Cell line | Schedule | CI at $ED_{50}$ |
|---|---|---|
| H358 | seliciclib/AG1478 | 0.96 |
|  | AG1478/seliciclib | 0.81 |
|  | seliciclib + AG1478 | 0.74 |

Seliciclib and AG1478 were tested in combination in the NSCLC cell line H358, using the protocol described in Methods and Materials. Concomitant (+) and sequential (/) treatment schedules were tested, and the resulting Combination Index values shown for $ED_{50}$ (the point on the curve where cellular proliferation is inhibited by 50%). Results are the average of at least three independent experiments. The CI values definitions are: 1.45-1.2 is moderately antagonistic, 1.2-1.1 is slightly antagonistic, 1.1-0.9 is additive, 0.9-0.85 is slightly synergistic, 0.85-0.7 is moderately synergistic, 0.7-0.3 is synergistic.

TABLE 3

Combinations of (i) seliciclib or the second generation inhibitors [1]-[4], and (ii) EGFR inhibitors AG1478, erlotinib, gefitinib or lapatinib, in H292 cells

| Drug Combination | AG1478 | Erlotinib | Gefitinib | Lapatinib |
|---|---|---|---|---|
| Seliciclib | 0.38 | 0.68 | 0.53 | 0.57 |
| [1] | 0.42 | 0.71 | 0.50 | 0.69 |
| [2] | 0.26 | 0.62 | 0.54 | 0.79 |
| [3] | 0.31 | 0.68 | 0.49 | 0.76 |
| [4] | 0.36 | 0.87 | 0.55 | 0.59 |

[1]: (3R)-3-{9-isopropyl-6-[(pyridin-3-ylmethyl)-amino]-9H-purin-2-ylamino}-2-methyl-pentan-2-ol.
[2]: (3S)-3-{9-isopropyl-6-[(pyridin-3-ylmethyl)-amino]-9H-purin-2-ylamino}-2-methyl-pentan-2-ol.
[3]: (2R3S)-3-{9-isopropyl-6-[(pyridin-3-ylmethyl)-amino]-9H-purin-2-ylamino}-pentan-2-ol.
[4]: (2R,3S-3-(6-((4,6-dimethylpyridin-3-ylmethylamino)-9-isopropyl-9H-purin-2-ylamino)pentan-2-ol

TABLE 4

Seliciclib or compound [4] in combination with lapatinib in the Her2 over expressing breast cancer cell line SkBr3

| Drug Combination | Lapatinib |
|---|---|
| Seliciclib | 0.72 |
| [4] | 0.67 |

References

1. Dancey, J. and E. A. Sausville, *Issues and progress with protein kinase inhibitors for cancer treatment.* Nature Reviews Drug Discovery, 2003. 2: p. 296-313.
2. Kantarjian, H., et al., *Hematologic and Cytogenetic Responses to Imatinib Mesylate in Chronic Myelogenous Leukemia.* N Engl J Med, 2002. 346(9): p. 645-652.
3. Harari, D. and Y. Yarden, *Molecular mechanisms underlying ErbB2/HER2 action in breast cancer.* Oncogene, 2000. 19(53): p. 6102-14.
4. Slamon, D. J., et al., *Human breast cancer: correlation of relapse and survival with amplification of the HER-2/neu oncogene.* Science, 1987. 235(4785): p. 177-82.
5. Tortora, G. and F. Ciardiello, *Anti-epidermal growth factor receptor drugs in cancer therapy.* Expert Opinion on Investigational Drugs, 2002. 11(6): p. 755-768.
6. Salomon, D. S., et al., *Epidermal growth factor-related peptides and their receptors in human malignancies.* Crit. Rev Oncol Hematol., 1995. 19(3): p. 183-232.
7. Silvestri, G. A. and M. P. Rivera, *Targeted Therapy for the Treatment of Advanced Non-small Cell Lung Cancer: A Review of the Epidermal Growth Factor Receptor Antagonists* 10.1378/chest.128.6.3975. Chest, 2005. 128(6): p. 3975-3984.
8. Shapiro, G. I., *Cyclin-dependent kinase pathways as targets for cancer treatment.* J Clin Oncol., 2006. 24(11): p. 1770-83.
9. Senderowicz, A. M., *Small-molecule cyclin-dependent kinase modulators.* Oncogene, 2003. 22: p. 6609-6620.
10. Shapiro, G. I. and J. W. Harper, *Anticancer drug targets: cell cycle and checkpoint control.* Journal of Clinical Investigation, 1999. 104(12): p. 1645-1653.
11. MacCallum, D. E., et al., *Seliciclib (CYC202, R-Roscovitine) Induces Cell Death in Multiple Myeloma Cells by Inhibition of RNA Polymerase II-Dependent Transcription and Down-regulation of Mcl-1.* Cancer Res, 2005. 65(12): p. 5399-5407.
12. Whittaker, S. R., et al., *The Cyclin-dependent kinase inhibitor CYC202 (R-roscovitine) inhibits retinoblastoma protein phosphorylation, causes loss of Cyclin D1, and activates the mitogen-activated protein kinase pathway.* Cancer Research, 2004. 64(1): p. 262-272.
13. Schubert, K. M. and V. Duronio, *Distinct roles for extracellular-signal-regulated protein kinase (ERK) mitogen-activated protein kinases and phosphatidylinositol 3-kinase in the regulation of Mcl-1 synthesis.* Biochemical journal, 2001. 356: p. 473-480.
14. Carlson, B., et al., *Down-regulation of cyclin D1 by transcriptional repression in MCF-7 human breast carcinoma cells induced by flavopiridol.* Cancer Res., 1999. 59(18): p. 4634-41.
15. Wu, K., et al., *Flavopiridol and trastuzumab synergistically inhibit proliferation of breast cancer cells: association with selective cooperative inhibition of cyclin D1-dependent kinase and Akt signaling pathways.* Molecular Cancer Therapeutics, 2002. 1(9): p. 695-706.
16. Nahta, R., et al., *Rate-limiting effects of Cyclin D1 in transformation by ErbB2 predicts synergy between herceptin and flavopiridol.* Cancer Research, 2002. 62(8): p. 2267-71.
17. Nahta, R., et al., *Epidermal growth factor receptor expression is a candidate target of the synergistic combination of trastuzumab and flavopiridol in breast cancer.* Cancer Research, 2003. 63(13): p. 3626-31.
18. Osherov, N. and A. Levitzki, *Epidermal-growth-factor-dependent activation of the src-family kinases.* Eur J. Biochem., 1994. 225(3): p. 1047-53.
19. Chou, T. C. and P. Talalay, *Quantitative analysis of dose-effect relationships: the combined effects of multiple drugs or enzyme inhibitors.* Adv Enzyme Regul, 1984. 22: p. 27-55.
20. Dancey, J. E. and H. X. Chen, *Strategies for optimizing combinations of molecularly targeted anticancer agents.* 2006. 5(8): p. 649-659.

21. Lee, R. J., et al., *Cyclin D1 is required for transformation by activated Neu and is induced through an E2F-dependent signaling pathway.* Mol Cell Biol., 2000. 20(2): p. 672-83.
22. Yu, Q., Y. Gaeng, and P. Sicinski, *Specific protection against breast cancers by cyclin D1 ablation.* Nature, 2001. 411(6841): p. 1017-1021.
23. Landis, M. W., et al., *Cyclin D1-dependent kinase activity in murine development and mammary tumorigenesis.* Cancer Cell, 2006. 9(1): p. 13-22.
24. Longva, K. E., et al., *Herceptin-induced inhibition of ErbB2 signaling involves reduced phosphorylation of Akt but not endocytic down-regulation of ErbB2.* Int J Cancer., 2005. 116(3): p. 359-67.
25. Ljungman, M. and M. T. Paulsen, *The cyclin-dependent kinase inhibitor roscovitine inhibits RNA synthesis and triggers nuclear accumulation of p53 that is unmodified at Ser15 and Lys382.* Mol Pharmacol, 2001. 60(4): p. 785-9.
26. Dubois, M. F., et al., *Inhibitors of transcription such as 5,6-dichloro-1-beta-D-ribofuranosylbenzimidazole and ioquinoline sulphonamide derivatives (H-8 and H-7) promote dephosphorylation of the carboxyl-terminal domain of RNA polymerase II largest subunit.* Journal of biological chemistry, 1994. 269: p. 13331-13336.
27. Scott, G. K., et al., *Transcriptional repression of ErbB2 by histone deacetylase inhibitors detected by a genomically integrated ErbB2 promoter-reporting cell screen.* Mol Cancer Ther., 2002. 1(6): p. 385-92.
28. Levitzki, A. and A. Gazit, *Tyrosine kinase inhibition: an approach to drug development.* Science, 1995. 267(5205): p. 1782-8.
29. Shepherd, F. A., et al., *Erlotinib in Previously Treated Non-Small-Cell Lung Cancer.* N Engl J Med, 2005. 353(2): p. 123-132.
30. Thomson, S., et al., *Epithelial to mesenchymal transition is a determinant of sensitivity of non-small-cell lung carcinoma cell lines and xenografts to epidermal growth factor receptor inhibition.* Cancer Res., 2005. 65(20): p. 9455-62.
31. Janmaat, M. L., et al., *Response to Epidermal Growth Factor Receptor Inhibitors in Non-Small Cell Lung Cancer Cells: Limited Antiproliferative Effects and Absence of Apoptosis Associated with Persistent Activity of Extracellular Signal-regulated Kinase or Akt Kinase Pathways.* Clin Cancer Res, 2003. 9(6): p. 2316-2326.
32. Kalish, L. H., et al., *Deregulated Cyclin D1 Expression Is Associated with Decreased Efficacy of the Selective Epidermal Growth Factor Receptor Tyrosine Kinase Inhibitor Gefitinib in Head and Neck Squamous Cell Carcinoma Cell Lines* 10.1158/1078-0432.CCR-04-0012. Clin Cancer Res, 2004. 10(22): p. 7764-7774.
33. Petty, W. J., et al., *Epidermal growth factor receptor tyrosine kinase inhibition represses cyclin D1 in aerodigestive tract cancers.* Clin Cancer Res., 2004. 10(22): p. 7547-54.
34. McClue, S., et al., *In vitro and in vivo antitumour propertiess of the cyclin dependent kinase inhibitor CYC202 (R-roscovitine).* International journal of cancer, 2002. 102 (463-468).
35. Chinnaiyan, P., et al., *Mechanisms of enhanced radiation response following epidermal growth factor receptor signaling inhibition by erlotinib (Tarceva).* Cancer Res., 2005. 65(8): p. 3328-35.
36. Huang, S., et al., *Dual-agent molecular targeting of the epidermal growth factor receptor (EGFR): combining anti-EGFR antibody with tyrosine kinase inhibitor.* Cancer Res., 2004. 64(15): p. 5355-62.
37. Zhou, Y. and M. G. Brattain, *Synergy of epidermal growth factor receptor kinase inhibitor AG1478 and ErbB2 kinase inhibitor AG879 in human colon carcinoma cells is associated with induction of apoptosis.* Cancer Res., 2005. 65(13): p. 5848-56.
38. Yauch, R. L., et al., *Epithelial versus Mesenchymal Phenotype Determines In vitro Sensitivity and Predicts Clinical Activity of Erlotinib in Lung Cancer Patients* 10.1158/1078-0432.CCR-05-1492. Clin Cancer Res, 2005. 11(24): p. 8686-8698.

The invention claimed is:

1. A combination comprising (i) an ErbB inhibitor or a pharmaceutically acceptable salt thereof; and (ii) roscovitine or a pharmaceutically acceptable salt thereof; wherein the ErbB inhibitor is selected from the group consisting of AG1478, erlotinib, gefitinib, and lapatinib.

2. A combination according to claim 1 wherein roscovitine is R-roscovitine.

3. A pharmaceutical composition comprising a combination according to claim 1 and a pharmaceutically acceptable carrier, diluent or excipient.

4. A pharmaceutical product comprising (i) an ErbB inhibitor or a pharmaceutically acceptable salt thereof; and (ii) roscovitine or a pharmaceutically acceptable salt thereof; wherein the ErbB inhibitor is selected from the group consisting of AG1478, erlotinib, gefitinib, and lapatinib.

5. A pharmaceutical product according to claim 4 wherein roscovitine is R-roscovitine.

6. A pharmaceutical product according to claim 4 the form of a pharmaceutical composition comprising a pharmaceutically acceptable carrier, diluent or excipient.

7. A pharmaceutical product according to claim 4 for use in the treatment of a proliferative disorder.

8. A pharmaceutical product according to claim 7 wherein the proliferative disorder is cancer.

9. A pharmaceutical product according to claim 8 wherein the cancer is selected from lung cancer, head or neck cancer, ovarian cancer and breast cancer.

10. A pharmaceutical product according to claim 9 wherein the lung cancer is non-small cell lung cancer (NSCLC).

11. A method of treating a proliferative disorder selected from the group consisting of lung cancer, head neck cancer, ovarian cancer and breast cancer, said method comprising simultaneously, sequentially or separately administering to a subject having said proliferative disorder (i) an ErbB inhibitor or a pharmaceutically acceptable salt thereof; and (ii) roscovitine or a pharmaceutically acceptable salt thereof; wherein the ErbB inhibitor is selected from the group consisting of AG1478, erlotinib, gefitinib, and lapatinib.

12. A method according to claim 11 wherein the lung cancer is non-small cell lung cancer (NSCLC).

13. A method according to claim 11 which comprises administering roscovitine or a pharmaceutically acceptable salt thereof to said subject prior to sequentially or separately administering said ErbB inhibitor to said subject.

14. A method according to claim 11 which comprises administering said ErbB inhibitor to said subject prior to sequentially or separately administering roscovitine or a pharmaceutically acceptable salt thereof to said subject.

15. A method according to claim 11 wherein roscovitine is R-roscovitine.

16. A method according to claim 11 wherein roscovitine or a pharmaceutically acceptable salt thereof and said ErbB inhibitor or a pharmaceutically acceptable salt thereof are each administered in a therapeutically effective amount with respect to the individual components.

17. A method according to claim 11 wherein roscovitine or a pharmaceutically acceptable salt thereof and said ErbB inhibitor or a pharmaceutically acceptable salt thereof are each administered in a subtherapeutic amount with respect to the individual components.

18. A kit of parts comprising: (i) an ErbB inhibitor or a pharmaceutically acceptable salt thereof; and (ii) roscovitine or a pharmaceutically acceptable salt thereof; wherein the ErbB inhibitor is selected from the group consisting of AG1478, erlotinib, gefitinib, and lapatinib.

19. A kit according to claim 18 wherein roscovitine is R-roscovitine.

* * * * *

UNITED STATES PATENT AND TRADEMARK OFFICE
CERTIFICATE OF CORRECTION

PATENT NO. : 9,173,938 B2
APPLICATION NO. : 12/573358
DATED : November 3, 2015
INVENTOR(S) : Green et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 175 days.

Signed and Sealed this
Twenty-first Day of June, 2016

Michelle K. Lee
*Director of the United States Patent and Trademark Office*